United States Patent
Locke et al.

(10) Patent No.: US 10,724,110 B2
(45) Date of Patent: *Jul. 28, 2020

(54) SYSTEMS AND METHODS FOR ANALYZING VIRAL NUCLEIC ACIDS

(71) Applicant: Seven Bridges Genomics Inc., Cambridge, MA (US)

(72) Inventors: Devin Locke, Medford, MA (US); Piotr Szamel, Somerville, MA (US)

(73) Assignee: Seven Bridges Genomics Inc., Charlestown, MA (US)

(*) Notice: Subject to any disclaimer, the term of this patent is extended or adjusted under 35 U.S.C. 154(b) by 468 days.

This patent is subject to a terminal disclaimer.

(21) Appl. No.: 15/014,500

(22) Filed: Feb. 3, 2016

(65) Prior Publication Data

US 2017/0058365 A1    Mar. 2, 2017

Related U.S. Application Data

(60) Provisional application No. 62/212,888, filed on Sep. 1, 2015.

(51) Int. Cl.
| | | |
|---|---|---|
| *G01N 33/48* | (2006.01) | |
| *C12Q 1/70* | (2006.01) | |
| *G16B 30/00* | (2019.01) | |
| *C12Q 1/6809* | (2018.01) | |

(52) U.S. Cl.
CPC ........... *C12Q 1/701* (2013.01); *C12Q 1/6809* (2013.01); *C12Q 1/70* (2013.01); *G16B 30/00* (2019.02); *C12Q 2600/156* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,511,158 A | 4/1996 | Sims |
| 5,583,024 A | 12/1996 | McElroy et al. |
| 5,674,713 A | 10/1997 | McElroy et al. |
| 5,700,673 A | 12/1997 | McElroy et al. |
| 5,701,256 A | 12/1997 | Marr et al. |
| 6,054,278 A | 4/2000 | Dodge et al. |
| 6,210,891 B1 | 4/2001 | Nyren et al. |
| 6,223,128 B1 | 4/2001 | Allex et al. |
| 6,306,597 B1 | 10/2001 | Macevicz |
| 6,582,938 B1 | 6/2003 | Su et al. |
| 6,818,395 B1 | 11/2004 | Quake et al. |
| 6,828,100 B1 | 12/2004 | Ronaghi |
| 6,833,246 B2 | 12/2004 | Balasubramanian |
| 6,890,763 B2 | 5/2005 | Jackowski et al. |
| 6,911,345 B2 | 6/2005 | Quake et al. |
| 6,925,389 B2 | 8/2005 | Hitt et al. |
| 6,989,100 B2 | 1/2006 | Norton |
| 7,169,560 B2 | 1/2007 | Lapidus et al. |
| 7,232,656 B2 | 6/2007 | Balasubramanian et al. |
| 7,282,337 B1 | 10/2007 | Harris |
| 7,321,623 B2 | 1/2008 | Dambrackas |
| 7,483,585 B2 | 1/2009 | Brakus, Jr. |
| 7,577,554 B2 | 6/2009 | Lystad et al. |
| 7,580,918 B2 | 8/2009 | Chang et al. |
| 7,598,035 B2 | 10/2009 | Macevicz |
| 7,620,800 B2 | 11/2009 | Huppenthal et al. |
| 7,776,616 B2 | 8/2010 | Heath et al. |
| 7,809,509 B2 | 10/2010 | Milosavljevic |
| 7,835,871 B2 | 11/2010 | Kain et al. |
| 7,885,840 B2 | 2/2011 | Sadiq et al. |
| 7,917,302 B2 | 3/2011 | Rognes |
| 7,957,913 B2 | 6/2011 | Chinitz et al. |
| 7,960,120 B2 | 6/2011 | Rigatti et al. |
| 8,146,099 B2 | 3/2012 | Tkatch et al. |
| 8,165,821 B2 | 4/2012 | Zhang |
| 8,209,130 B1 | 6/2012 | Kennedy et al. |
| 8,340,914 B2 | 12/2012 | Gatewood et al. |
| 8,370,079 B2 | 2/2013 | Sorenson et al. |
| 8,639,847 B2 | 1/2014 | Blaszczak et al. |
| 2004/0023209 A1 | 2/2004 | Jonasson |
| 2005/0089906 A1 | 4/2005 | Furuta et al. |
| 2006/0024681 A1 | 2/2006 | Smith et al. |
| 2006/0195269 A1 | 8/2006 | Yeatman et al. |
| 2006/0292611 A1 | 12/2006 | Berka et al. |
| 2007/0087365 A1 | 4/2007 | Van Criekinge et al. |
| 2007/0114362 A1 | 5/2007 | Feng et al. |
| 2007/0166707 A1 | 7/2007 | Schadt et al. |

(Continued)

FOREIGN PATENT DOCUMENTS

| | | |
|---|---|---|
| KR | 101282798 B1 | 7/2013 |
| WO | 2007/086935 A2 | 8/2007 |

(Continued)

OTHER PUBLICATIONS

Neumann, T., 2005. Efficient generation and execution of DAG-structured query graphs (Doctoral dissertation, Universität Mannheim).*

(Continued)

*Primary Examiner* — Anna Skibinsky
(74) *Attorney, Agent, or Firm* — Wolf, Greenfield & Sacks, P.C.

(57) ABSTRACT

The invention provides systems and methods for analyzing viruses by representing viral genetic diversity with a directed acyclic graph (DAG), which allows genetic sequencing technology to detect rare variations and represent otherwise difficult-to-document diversity within a sample. Additionally, a host-specific sequence DAG can be used to effectively segregate viral nucleic acid sequence reads from host sequence reads when a sample from a host is subject to sequencing. Known viral genomes can be represented using a viral reference DAG and the viral sequence reads from the sample can be compared to viral DAG to identify viral species or strains from which the reads were derived. Where the viral sequence reads indicate great genetic diversity in the virus that was infecting the host, those reads can be assembled into a DAG that itself properly represents that diversity.

20 Claims, 11 Drawing Sheets

(56) References Cited

U.S. PATENT DOCUMENTS

| | | |
|---|---|---|
| 2008/0003571 A1 | 1/2008 | McKernan et al. |
| 2008/0077607 A1 | 3/2008 | Gatawood et al. |
| 2008/0251711 A1 | 10/2008 | Reilly |
| 2008/0281463 A1 | 11/2008 | Suh et al. |
| 2008/0294403 A1 | 11/2008 | Zhu et al. |
| 2009/0026082 A1 | 1/2009 | Rothberg et al. |
| 2009/0119313 A1 | 5/2009 | Pearce |
| 2009/0127589 A1 | 5/2009 | Rothberg et al. |
| 2009/0164135 A1 | 6/2009 | Brodzik et al. |
| 2009/0191565 A1 | 7/2009 | Lapidus et al. |
| 2009/0233809 A1 | 9/2009 | Faham et al. |
| 2009/0300781 A1 | 12/2009 | Bancroft et al. |
| 2009/0318310 A1 | 12/2009 | Liu et al. |
| 2009/0325145 A1 | 12/2009 | Sablon et al. |
| 2010/0010992 A1 | 1/2010 | Morris |
| 2010/0035252 A1 | 2/2010 | Rothberg et al. |
| 2010/0041048 A1 | 2/2010 | Diehl et al. |
| 2010/0137143 A1 | 6/2010 | Rothberg et al. |
| 2010/0169026 A1* | 7/2010 | Sorenson ............. G16B 30/00 702/20 |
| 2010/0188073 A1 | 7/2010 | Rothberg et al. |
| 2010/0197507 A1 | 8/2010 | Rothberg et al. |
| 2010/0240046 A1 | 9/2010 | Palmer et al. |
| 2010/0282617 A1 | 11/2010 | Rothberg et al. |
| 2010/0285578 A1 | 11/2010 | Selden et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0004413 A1 | 1/2011 | Carnevali et al. |
| 2011/0009278 A1 | 1/2011 | Kain et al. |
| 2011/0098193 A1 | 4/2011 | Kingsmore et al. |
| 2011/0207135 A1 | 8/2011 | Faham et al. |
| 2011/0257889 A1 | 10/2011 | Klammer et al. |
| 2012/0030566 A1 | 2/2012 | Victor |
| 2012/0040851 A1 | 2/2012 | Lieberman et al. |
| 2012/0041727 A1 | 2/2012 | Mishra et al. |
| 2012/0045771 A1 | 2/2012 | Beier et al. |
| 2012/0157322 A1 | 6/2012 | Myllykangas et al. |
| 2012/0239706 A1 | 9/2012 | Steinfadt |
| 2012/0330566 A1 | 12/2012 | Chaisson |
| 2013/0029879 A1 | 1/2013 | Shetty et al. |
| 2013/0035904 A1 | 2/2013 | Kuhn |
| 2013/0059738 A1 | 3/2013 | Leamon et al. |
| 2013/0059740 A1 | 3/2013 | Drmanac et al. |
| 2013/0073214 A1 | 3/2013 | Hyland et al. |
| 2013/0124100 A1 | 5/2013 | Drmanac et al. |
| 2013/0232480 A1 | 9/2013 | Winterfeldt et al. |
| 2013/0289099 A1 | 10/2013 | Goff et al. |
| 2013/0311106 A1 | 11/2013 | White et al. |
| 2013/0332081 A1 | 12/2013 | Reese et al. |
| 2013/0345066 A1 | 12/2013 | Brinza et al. |
| 2014/0012866 A1 | 1/2014 | Bowman et al. |
| 2014/0025312 A1 | 1/2014 | Chin et al. |
| 2014/0051588 A9 | 2/2014 | Drmanac et al. |
| 2014/0066317 A1 | 3/2014 | Talasaz |
| 2014/0129201 A1 | 5/2014 | Kennedy et al. |
| 2014/0136120 A1 | 5/2014 | Colwell et al. |
| 2014/0200147 A1 | 7/2014 | Bartha et al. |
| 2014/0278590 A1 | 9/2014 | Abbassi et al. |
| 2014/0280360 A1 | 9/2014 | Webber et al. |
| 2014/0281708 A1 | 9/2014 | Adam et al. |
| 2014/0323320 A1 | 10/2014 | Jia et al. |
| 2014/0371110 A1* | 12/2014 | Van Rooyen ..... H01L 21/76886 506/38 |
| 2015/0020061 A1 | 1/2015 | Ravi |
| 2015/0056613 A1 | 2/2015 | Kural |
| 2015/0057946 A1 | 2/2015 | Kural |
| 2015/0066383 A1 | 3/2015 | Wernicke |
| 2015/0094212 A1 | 4/2015 | Gottimukkala et al. |
| 2015/0110754 A1 | 4/2015 | Bai et al. |
| 2015/0112602 A1 | 4/2015 | Kural et al. |
| 2015/0112658 A1 | 4/2015 | Kural et al. |
| 2015/0197815 A1 | 7/2015 | Kural |
| 2015/0199472 A1 | 7/2015 | Kural |
| 2015/0199473 A1 | 7/2015 | Kural |
| 2015/0199474 A1 | 7/2015 | Kural |
| 2015/0199475 A1 | 7/2015 | Kural |
| 2015/0227685 A1 | 8/2015 | Kural |
| 2015/0293994 A1 | 10/2015 | Kelly |
| 2015/0302145 A1 | 10/2015 | Kural et al. |
| 2015/0310167 A1 | 10/2015 | Kural et al. |
| 2015/0344970 A1 | 12/2015 | Vogelstein et al. |
| 2015/0347678 A1 | 12/2015 | Kural |
| 2015/0356147 A1 | 12/2015 | Mishra et al. |
| 2016/0259880 A1 | 9/2016 | Semenyuk |
| 2016/0306921 A1 | 10/2016 | Kural |
| 2016/0342737 A1 | 11/2016 | Kaye |
| 2016/0355881 A1 | 12/2016 | Wangh et al. |
| 2016/0364523 A1 | 12/2016 | Locke et al. |
| 2017/0058320 A1 | 3/2017 | Locke et al. |
| 2017/0058341 A1 | 3/2017 | Locke et al. |
| 2017/0058365 A1 | 3/2017 | Locke et al. |
| 2017/0198351 A1 | 7/2017 | Lee et al. |
| 2017/0199959 A1 | 7/2017 | Locke |
| 2017/0199960 A1 | 7/2017 | Ghose et al. |
| 2017/0242958 A1 | 8/2017 | Brown |

FOREIGN PATENT DOCUMENTS

| | | |
|---|---|---|
| WO | 2010/010992 A1 | 1/2010 |
| WO | 2012/096579 A2 | 7/2012 |
| WO | 2012/098515 A1 | 7/2012 |
| WO | 2012/142531 A2 | 10/2012 |
| WO | 2013/035904 A1 | 3/2013 |
| WO | 2013043909 A1 | 3/2013 |
| WO | 2013/106737 A1 | 7/2013 |
| WO | 2013184643 A1 | 12/2013 |
| WO | 2015027050 A1 | 2/2015 |
| WO | 2015048753 A1 | 4/2015 |
| WO | 2015058093 A1 | 4/2015 |
| WO | 2015058095 A1 | 4/2015 |
| WO | 2015058097 A1 | 4/2015 |
| WO | 2015058120 A1 | 4/2015 |
| WO | 2015061099 A1 | 4/2015 |
| WO | 2015061103 A1 | 4/2015 |
| WO | 2015105963 A1 | 7/2015 |
| WO | 2015123269 A1 | 8/2015 |
| WO | 2016141294 A1 | 9/2016 |
| WO | 2016201215 A1 | 12/2016 |
| WO | 2017120128 A1 | 7/2017 |
| WO | 2017123864 A1 | 7/2017 |
| WO | 2017147124 A1 | 8/2017 |

OTHER PUBLICATIONS

Hendren, etal, 1990. Parallelizing programs with recursive data structures. IEEE Transactions on parallel and distributed systems, 1(1), pp. 35-47.*

Croft et al., Sep. 1991. The use of phrases and structured queries in information retrieval. In Proceedings of the 14th annual international ACM SIGIR conference on Research and development in information retrieval (pp. 32-45). ACM.*

Smith et al., "Identification of Common Molecular Subsequences," J. Mol. Biol. (1981) vol. 147, pp. 195-197.*

Yanovsky, V., Rumble, S.M. and Brudno, M., (Sep. 2008) Read mapping algorithms for single molecule sequencing data. In International Workshop on Algorithms in Bioinformatics (pp. 38-49). Springer, Berlin, Heidelberg.*

Pruesse et al. "SINA: Accurate high-throughput multiple sequence alignment of ribosomal RNA genes" (Bioinformatics, vol. 28 (2012) pp. 1823-1829).*

Lee et al. "Multiple sequence alignment using partial order graphs" (Bioinformatics, vol. 18 (2002) pp. 452-462).*

Wu, 2010, Fast and SNP-tolerant detection of complex variants and splicing in short reads, Bioinformatics, 26(7):873-881.

Xing, 2006, An expectation-maximization algorithm for probabilistic reconstructions of full-length isoforms from splice graphs, Nucleic Acids Research, 34:3150-3160.

Yang, 2013, Leveraging reads that span multiple single nucleotide polymorphisms for haplotype inference from sequencing data, Bioinformatics 29(18):2245-2252.

(56) References Cited

OTHER PUBLICATIONS

Yang, 2014, Community detection in networks with node attributes, proc IEEE ICDM '13, arXiv:1401.7267.
Yanovsky, 2008, Read mapping algorithms for single molecule sequencing data, Proc 8th Int Workshop Alg Bioinformatics 5251:38-49.
Yildiz, 2014, BIFI: a Taverna plugin for a simplified and user-friendly workflow platform, BMC Res Notes 7:740.
Yu, 2007, A tool for creating and parallelizing bioinformatics pipelines, DOD High Performance Computing Conf 417-420.
Yu, 2010, The construction of a tetraploid cotton genome wide comprehensive reference map, Genomics 95:230-240.
Zhang, 2013, Taverna Mobile: Taverna workflows on Android, EMBnet J 19(B):43-45.
Zhao, 2012, Why Workflows Break—Understanding and Combating Decay in Taverna Workflows, eScience 2012, Chicago, Oct. 2012.
BCF2 Quick Reference (r198), available at http://samtools.github.io/hts-specs/BCFv2_qref.pdf.
Durbin, 2014, Efficient haplotype matching and storage using the positional Burrows-Wheeler transform (PBWT), Bioinformatics 30(9):1266-1272.
Layer, 2015, Efficient genotype compression and analysis of large genetic-variation data sets, Nat Meth 13(1):63-65.
Layer, 2015, Efficient compression and analysis of large genetic variation datasets, Biorxiv preprint, available at http://biorxiv.org/content/early/2015/04/20/018259.
Li, 2015, BGT: efficient and flexible genotype query across many samples, arXiv:1506.08452 [q-bio.GN].
Li, 2015, Towards Better Understanding of Artificats in Variant Calling from High-Coverage Samples, arXiv:1404.0929 [q-bio.GN].
Popitsch, 2013, NGC: lossless and lossy compression of aligned high-throughput sequencing data, Nucl Acids Res, 41(1):e27.
Sudmant, 2015, An integrated map of structural variation in 2,504 human genomes, Nature 526:75-81.
Tewhey, 2011, The importance of phase information for human genomics, Nat Rev Gen 12:215-223.
The Variant Call Format (VCF) Version 4.2 Specification (Jan. 26, 2015), available at https://samtools.github.io/hts-specs/VCFv4.2.pdf.
Grasso, 2004, Combining partial order alignment and progressive multiple sequence alignment increases alignment speed and scalability to very large alignment problems, Bioinformatics 20(10):1546-1556.
Rajaram, 2013, Pearl millet [*Pennisetum glaucum* (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Robertson, 2010, De novo assembly and analysis of RNA-seq data, Nat Meth 7(11):909.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with intersequence SIMD parallelisation, Bioinformatics 12:221.
Ronquist, 2012, MrBayes 3.2: efficient Bayesian phylogenetic inference and model choice across a large model space, Syst Biol 61(3):539-42.
Rothberg, 2011, An integrated semiconductor device enabling non-optical genome sequencing, Nature 475:348-352.
Swim, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schenk, 2013, A pipeline for comprehensive and automated processing of electron diffraction data in IPLT, J Struct Biol 182(2):173-185.
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5)596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Sroka, 2006, XQTav: an XQuery processor for Taverna environment, Bioinformatics 22(10):1280-1.
Sroka, 2010, A formal semantics for the Taverna 2 workflow model, J Comp Sys Sci 76(6):490-508.
Sroka, 2011, CalcTav—integration of a spreadsheet and Taverna workbench, Bioinformatics 27(18):2618-9.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing.pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tan, 2010, A Comparison of Using Taverna and BPEL in Building Scientific Workflows: the case of caGrid, Concurr Comput 22(9):1098-1117.
Tan, 2010, CaGrid Workflow Toolkit: a Taverna based workflow tool for cancer grid, BMC Bioinformatics 11:542.
Tarhio, 1993, Approximate Boyer-Moore String Matching, SIAM J Comput 22(2):243-260.
The 1000 Genomes Project, 2015, A global reference for human genetic variation, Nature 526:68-74.
Thomas, 2014, Community-wide effort aims to better represent variation in human reference genome, Genome Web (11 pages).
Torri, 2012, Next generation sequence analysis and computational genomics using graphical pipeline workflows, Genes (Basel) 3(3):545-575.
Trapnell, 2009, TopHat: discovering splice junctions with RNA-Seq, Bioinfomiatics 25:1105-1111.
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.

(56) References Cited

OTHER PUBLICATIONS

Truszkowski, 2011, New developments on the cheminformatics open workflow environment CDK-Taverna, Cheminform 3:54.
Turi, 2007, Taverna Workflows: Syntax and Semantics, IEEE Int Conf on e-Science and Grid Computing 441-448.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Wassink, 2009, Using R in Taverna: RShell v1.2. BMC Res Notes 2:138.
Waterman, 1976, Some biological sequence metrics, Adv Math 20(3):367-387.
Wellcome Trust Case Control Consortium, 2007, Genome-wide association study of 14,000 cases of seven common diseases and 3,000 shared controls, Nature 447:661-678.
Wolstencroft, 2005, Panoply of Utilities in Taverna, Proc 2005 1st Int Conf e-Science and Grid Computing 156-162.
Wolstencroft, 2013, The Taverna Workflow Suite: Designing and Executing Workflows of Web Services on the Desktop, Web or in the Cloud, Nucl Acids Res 41(W1):W556-W561.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol. 6(6):649-668.
Hokamp, 2003, Wrapping up BLAST and Other Applications for Use on Unix Clusters, Bioinformatics 19(3)441-42.
Holland, 2008, BioJava: an open-source framework for bioinformatics, Bioinformatics 24(18):2096-2097.
Homer, 2010, Improved variant discovery through local re-alignment of short-read next generation sequencing data using SRMA, Genome Biol 11(10):R99.
Hoon, 2003, Biopipe: A flexible framework for protocol-based bioinformatics analysis, Genome Res 13(8):1904-1915.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hull, 2006, Taverna: a tool for building and running workflows of services, Nucl Acids Res 34(Web Server issue): W729-32.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).
International Search Report and Written Opinion dated Jan. 5, 2016, for International Patent Application PCT/US2015/054461 with International Filing Date Oct. 7, 2015 (7 pages).
International Search Report and Written Opinion dated Mar. 19, 2015, for International Application No. PCT/US2014/061162 with International Filing Date Oct. 17, 2014 (12 pages).
International Search Report and Written Opinion dated May 11, 2015, for International Patent Application No. PCT/US2015/015375 with International Filing Date Feb. 11, 2015 (12 pages).
International Search Report and Written Opinion dated May 5, 2016, for International Patent Application No. PCT/US2016/020899, wiht International Filing Date Mar. 4, 2016 (12 pages).
International Search Report and Written Opinion dated Dec. 11, 2014, for International Patent Application No. PCT/US14/52065, filed Aug. 21, 2014, (18 pages)
International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
Search Report and Written Opinion of the International Searching Authority dated Nov. 17, 2015 for International Application No. PCT /US2015/048891 (11 Pages).
Kano, 2010, Text mining meets workflow: linking U-Compare with Taverna, Bioinformatics 26(19):2486-7.
Katoh, 2005, MAFFT version 5: improvement in accuracy of multiple sequence alignment, Nucl Acids Res 33(2):511-518.
Kawas, 2006, BioMoby extensions to the Taverna workflow management and enactment software, BMC Bioinformatics 7:523.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Krabbenhoft, 2008, Integrating ARC grid middleware with Taverna workflows, Bioinformatics 24(9):1221-2.
Kuhn, 2010, CDK-Taverna: an open workflow environment for cheminformatics, BMC Bioinformatics 11:159.
Kumar, 2010, Comparing de novo assemblers for 454 transcriptome data, BMC Genomics 11:571.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Lanzen, 2008, The Taverna Interaction Service: enabling manual interaction in workflows, Bioinformatics 24(8):1118-20.
Larkin, 2007, Clustal W and Clustal X version 2.0, Bioinformatics 23(21):2947-2948.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, MOSAIK: A hash-based algorithm for accurate next-generation sequencing short-read mapping, PLoS One 9(3):e90581.

(56) References Cited

OTHER PUBLICATIONS

LeGault, 2010, Learning Probalistic Splice Graphs from RNA-Seq data, pages.cs.wisc.edu/~legault/cs760_writeup.pdf; retrieved from the Internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, Automated manipulation of systems biology models using libSBML within Taverna workflows, Bioinformatics 24(2):287-9.
Li, 2008, Performing statistical analyses on quantitative data in Taverna workflows: an example using R and maxdBrowse to identify differentially-expressed genes from microarray data, BMC Bioinformatics 9:334.
Li, 2008, SOAP: short oligonucleotide alignment program, Bioinformatics 24(5):713-14.
Li, 2009, Fast and accurate short read alignment with Burrows-Wheeler Transform. Bioinformatics 25:1754-60.
Li, 2009, SOAP2: an improved ultrafast tool for short read alignment, Bioinformatics 25(15):1966-67.
Li, 2009, The Sequence Alignment/Map format and SAMtools, Bioinformatics 25(16):2078-9.
Li, 2010, A survey of sequence alignment algorithms for next-generation sequencing, Briefings in Bionformatics 11(5):473-483.
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Boinf 12:10.
Ma, 2010, Multiple genome alignment based on longest path in directed acyclic graphs, Int J Bioinformatics 6(4):366-683.
Machine translation of KR 10-1282798 B1 generated on Jan. 6, 2016, by the website of the European Patent Office (23 pages).
Machine translation produced on Jun. 1, 2015, by Espacenet of WO 2010/010992 A1 (11 pages).
Machine translation produced on Jun. 1, 2015, by WPIO website of WO 2013/035904 (10 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retrieved from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
Mazrouee, 2014, FastHap: fast and accurate single individual haplotype reconstructions using fuzzy conflict graphs, Bioinformatics 30:i371-i378.
McKenna, 2010, The Genome Analysis Toolkit: a MapReduce framework for analyzing next-generation DNA sequencing data, Genome Res 20(9):1297-1303.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Missier, 2010, Taverna, reloaded, Proc. Scientific and Statistical Database Management, 22nd Int Conf, Heidelberg, Germany, Jun./Jul. 2010, Gertz & Ludascher, Eds., Springer.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
Nenadic, 2010, Nested Workflows, The Taverna Knowledge Blog, Dec. 13, 2010. Retrieved on Feb. 25, 2016 from http://taverna.knowledgeblog.org/2010/12/13/nested-workflows/.
Newman, 2013, Community detection and graph portioning, Europhys Lett 103(2):28003, arXiv:1305.4974v1.
Ning, 2001, SSAHA: a fast search method for large DNA databases, Genome Res 11(10):1725-9.
O'Rawe, 2013, Low Concordance of Multiple Variant-Calling Pipelines: Practical Implications for Exome and Genome Sequencing, Genome Med 5:28.
Oinn, 2004, Taverna: a tool for the composition and enactment of bioinformatics workflows, Bioinformatics 20(17):3045-54.
Oinn, 2006, Taverna: lessons in creating a workflow environment for the life sciences, Concurrency and Computation: Practice and Experience 18(10):1067-1100.
Oshlack, 2010, From RNA-seq reads to differential expression results. Genome Bio 11:220.
Pabinger, 2013, A survey of tools for variant analysis of next-generation genome sequencing data, Brief Bioinf.
Paterson, 2009, An XML transfer schema for exchange of genomic and genetic mapping data: implementation as a web service in a Taverna workflow, BMC Bioinformatics 10:252.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Peixoto, 2014, Efficient Monte Carlo and greedy heuristic for the inference of stochastic block models, Phys. Rev. E 89, 012804.
Pope, 2014, ROVER Variant Caller: Read-Pair Overlap Considerate Variant-Calling Software Applied to PCR-Based Massively Parallel Sequencing Datasets, Source Code Bio Med 9:3.
Posada, 1998, MODEL TEST: testing the model of DNA substitution, Bioinfomiatics 14(9):817-8.
Potter, 1994, ASC: An Associative-Computing Paradigm, Computer 27(11):19-25.
Potter, 2004, The ensemble analysis pipeline, Genome Res 14:934-941.
Quail, et al., 2012, A tale of three next generation sequencing platforms: comparison of Ion Torrent, Pacific Biosciences and Illumina MiSeq sequencers, BMC Genomics 13:341.
Abouelhoda, 2012, Tavaxy: integrating Taverna and Galaxy workflows with cloud computing support, BMC Bioinformatics 13:77.
Agarwal, 2013, SINNET: Social Interaction Network Extractor from Text, Proc IJCNLP 33-36.
Aguiar, 2012, HapCompass: A fast cycle basis algorithm for accurate haplotype assembly of sequence data, J Comp Biol 19(6):577-590.
Aguiar, 2013, Haplotype assembly in polyploid genomes and identical by descent shared tracts, BioInformatics 29(13):i352-i360.
Airoldi, 2008, Mixed membership stochastic blockmodels, JMLR 9:1981-2014.
Altera, 2007, Implementation of the Smith-Waterman algorithm on reconfigurable supercomputing platform, White Paper ver 1.0 (18 pages).

(56) References Cited

OTHER PUBLICATIONS

Altschul, 1986, Optimal Sequence Alignment Using Affine Gap Costs, Bull Math Biol 48(5/6):603-616.
Bansal, 2008, An MCMC algorithm for haplotype assembly from whole-genome sequence data, Genome Res 18:1336-1346.
Bao, 2013, BRANCH: boosting RNA-Seq assemblies with partial or related genomic sequences, Bioinformatics 29(10):1250-1259.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages); retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Clark, 2014, Illumina announces landmark $1,000 human genome sequencing, Wired, Jan. 15, 2014.
Cock, 2013, Galaxy tools and workflows for sequence analysis with applications in molecular plant pathology, Peer J 1: e167.
Cohen-Boulakia, 2014, Distilling structure in Taverna scientific workflows: a refactoring approach, BMC Bioinformatics 15(Suppl 1):S12.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Danecek, 2011, The variant call format and VCFtools, Bioinformatics 27(15):2156-2158.
Delcher, 1999, Alignment of whole genomes, Nucl. Acids Res 27(11):2369-76.
DePristo, 2011, A framework for variation discovery and genotyping using next-generation DNA sequencing data, Nat Gen 43:491-498.
Dinov, 2011, Applications of the pipeline environment for visual informatics and genomic computations, BMC Bioinformatics 12:304.
Dudley, 2009, A quick guide for developing effective bioinformatics programming skills, PLoS Comput Biol 5(12): e1000589.
Durham, 2005, EGene: a configurable pipeline system for automated sequence analysis, Bioinformatics 21(12):2812-2813.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Glusman, 2014, Whole-genome haplotyping approaches and genomic medicine, Genome Med 6:73.
Goto, 2010, BioRuby: bioinformatics software for the Ruby programming language, Bioinformatics 26(20):2617-2619.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harenberg, 2014, Community detection in large-scale networks: a survey and empirical evaluation, WIREs Comp Stat 6:426-439.
Harrow, 2012, GENCODE: The reference human genome annotation for the Encode Project, Genome Res 22:1760-1774.
He, 2010, Optimal algorithms for haplotype assembly from whole-genome sequence data, Bioinformatics 26:i183-i190.
Albers, 2011, Dindel: Accurate indel calls from short-read data, Genome Research 21:961-973.
Alioto et al., A comprehensive assessment of somatic mutation detection in cancer using whole-genome sequencing, Nature Communications, Dec. 9, 2015.
Barbieri, 2013, Exome sequencing identifies recurrent SPOP, FOXA1 and MED12 mutations in prostate cancer, Nature Genetics 44:6 685-689.
Beerenwinkel, 2007, Conjunctive Bayesian Networks, Bernoulli 13(4), 893-909.
Browning et al, Haplotype phasing: existing methods and new developments, 2011, vol. 12, Nature Reviews Genetics.
Caboche et al, Comparison of mapping algorithms used in high-throughput sequencing: application to Ion Torrent data, 2014, vol. 15, BMC Genomics.
Cartwright, DNA assembly with gaps (DAWG): simulating sequence evolution, 2005, pp. iii31-iii38, vol. 21, Oxford University Press.
Craig, 1990, Ordering of cosmid clones covering the Herpes simplex virus type I (HSV-I) genome: a test case for fingerprinting by hybridisation, Nucleic Acids Research 18:9 pp. 2653-2660.
Denoeud, 2004, Identification of polymorphic tandem repeats by direct comparison of genome sequence from different bacterial strains: a web-based resource, BMC Bioinformatics 5:4 pp. 1-12.
Duan et al., Optimizing de novo common wheat transcriptome assembly using short-read RNA-Seq data. (2012) pp. 1-12, vol. 13, BMC Genomics.
Exam Report issued in EP14803268.3.
Examination Report issued in SG 11201601124Y.
Extended European Search Report issued in EP 14837955.5.
Extended European Search Report issued in EP 14847490.1.
Extended European Search Report issued in EP 14854801.9.
Gerlinger, 2012, Intratumor Heterogeneity and Branched Evolution Revealed by Multiregion Sequencing, 366:10 883-892.
Golub, 1999, Molecular classification of cancer: class discovery and class prediction by gene expression monitoring, Science 286, pp. 531-537.
International Search Report and Written Opinion dated Aug. 31, 2017, for International Application No. PCT/US2017/018830 with International Filing Date Feb. 22, 2017, (11 pages).

(56) References Cited

OTHER PUBLICATIONS

International Search Report and Written Opinion dated Apr. 19, 2017 for International Patent Application No. PCT/US2017/012015, (14 Pages).
International Search Report and Written Opinion dated Jan. 10, 2017, for International Patent Application No. PCT/US16/57324 with International Filing Date Oct. 17, 2016, (7 pages).
International Search Report and Written Opinion dated Apr. 7, 2017, for International Patent Application No. PCT/US17/13329, filed Jan. 13, 2017, (9 pages).
International Search Report and Written Opinion dated Feb. 4, 2015, for International Patent Application No. PCT/US2014/061198, filed Oct. 17, 2014, (8 pages).
International Search Report and Written Opinion dated Feb. 10, 2015, for International Patent Application No. PCT/US2014/060690, filed Oct. 15, 2014, PCT/US2014/060690 (11 pages).
Koolen, 2008, Clinical and Molecular Delineation of the 17q21.31 Microdeletion Syndrome, J Med Gen 45(11):710-720.
Lecca, 2015, Defining order and timing of mutations during cancer progression: the TO-DAG probabilistic graphical model, Frontiers in Genetics, vol. 6 Article 309 1-17.
Lee et al. Accurate read mapping using a graph-based human pan-genome. (May 2015) American Society of Human Genetics 64th Annual Meeting Platform Abstracts; Abstract 41.
Lee, 2014, Accurate read mapping using a graph-based human pan-genome, ASHG 2014 Abstracts.
Lupski, 2005, Genomic disorders: Molecular mechanisms for rearrangements and conveyed phenotypes, PLoS Genetics 1(6):e49.
Marth et al., 1999—A general approach to single-nucleotide polymorphism discovery, pp. 452-456, vol. 23, Nature Genetics.
Mourad, 2012, A hierarchical Bayesian network approach for linkage disequilibrium modeling and data-dimensionality reduction prior to genome-wide association studies, BMC Bioinformatics 12:16 1-20.
Myers, The Fragment Assembly String Graph, Bioinformatics, 2005, pp. ii79-ii85, vol. 21.
Newman, 2014, An ultrasensitive method for quantitating circulating tumor DNA with broad patient coverage, Nature Medicine 20:5 1-11.
Olsson, 2015, Serial monitoring of circulating tumor DNA in patients with primary breast cancer for detection of occult metastatic disease, EMBO Molecular Medicine 7:8 1034-1047.
Parks, 2015, Detecting non-allelic homologous recombination from high-throughput sequencing data, Genome Biol 16:17.
Pop et al., 2004, Comparative genome assembly, Briefings in Bioinformatics vol. 5, pp. 237-248.
Pruesse, 2012, SINA: Accurate high-throughput multiple sequence alignment of ribosomal RNA genes, Bioinformatics 28:14 1823-1829.
Sturgeon, RCDA: a highly sensitive and specific alternatively spliced transcript assembly tool featuring upstream consecutive exon structures, Genomics, Dec. 2012, 100(6): 357-362.
Uchiyama et al., CGAT: a comparative genome analysis tool for visualizing alignments in the analysis of complex evolutionary changes between closely related genomes, 2006, e-pp. 1-17, vol. 7:472; BMC Bioinformatics.
Written Opinion issued in SG 11201601124Y.
Written Opinion issued in SG 11201602903X.
Written Opinion issued in SG 11201603039P.
Written Opinion issued in SG 11201603044S.
Written Opinion issued in SG 11201605506Q.
Zeng, 2013, PyroHMMvar: a sensitive and accurate method to call short indels and SNPs for Ion Torrent and 454 data, Bioinformatics 29:22 2859-2868.
Zhang et al., Construction of a high-density genetic map for sesame based on large scale marker development by specific length amplified fragment (SLAF) sequencing. (2013) pp. 1-12, vol. 13, BMC Plant Biology.
U.S. Appl. No. 15/007,865, filed Jan. 27, 2016, Locke et al.
U.S. Appl. No. 14/994,758, filed Jan. 13, 2016, Locke et al.
U.S. Appl. No. 15/007,874, filed Jan. 27, 2016, Locke et al.
U.S. Appl. No. 15/014,483, filed Feb. 3, 2016, Locke et al.
Cormen et al., Introduction to Algorithms. Third Edition. The MIT Press. 2009. 6 pages.
Crochemore et al., Direct Construction of Compact Directed Acyclic Word Graphs. Springer, Berlin, Heidelberg. 1997:116-29.
Do et al., Compressed Directed Acyclic Word Graph with Application in Local Alignment. Algorithmica. 2013;67:125-41.
Jones et al., AliWABA: alignment on the web through an A-Bruijn approach. Nucleic Acids Research. 2006;34:613-6.
Kim et al., Introducing EzTaxon-e: a prokaryotic 16S rRNA gene sequence database with phylotypes that represent uncultured species. International Journal of Systematic and Evolutionary Microbiology. 2012;62:716-21.
Quast et al., The SILVA ribosomal RNA gene database project: improved data processing and web-based tools. Nucleic Acids Research. 2013;41:590-6.
Schmieder et al., Identification and removal of ribosomal RNA sequences from metatranscriptomes. Bioinformatics. 2012;28(3):433-5.
Standish, Data Structures, Algorithms and Software Principles in C. Chapter 10 Section 10.1: Introduction and Motivation and Section 10.2: Basic Concepts and Terminology. Addison-Wesley Publishing Company. 1995:405-411.
Wajid et al., Review of General Algorithmic Features for Genome Assembles for Next Generation Sequencers. Genomics Proteomics and Bioinformatics. Science Direct. Elsevier. 2012;10:58-73.
Wheeler et al., the complete genome of an individual by massively parallel DNA sequencing. Nature. Letters. 2008;452:872-6.
U.S. Appl. No. 15/014,500, filed Feb. 3, 2016, Locke et al.
Floyd, Algorithm 245: treesort. Communications of the ACM. Dec. 1, 1964;7(12):701.
Huddleston et al., A new data structure for representing sorted lists. Acta informatica. Jun. 1, 1982;17(2):157-84.

\* cited by examiner

FIG. 9

SYSTEMS AND METHODS FOR ANALYZING VIRAL NUCLEIC ACIDS

CROSS-REFERENCE TO RELATED APPLICATIONS

This application claims priority to, and the benefit of, U.S. Provisional Application Ser. No. 62/212,888, filed Sep. 1, 2015, the contents of which are incorporated by reference.

TECHNICAL FIELD

The invention relates to viral genomics.

BACKGROUND

If a person is suspected of having a viral infection that is potentially dangerous, the safest action for the public is to quarantine the infected person. Unfortunately, it is difficult to tell whether the infection is from a particularly dangerous strain of a virus by observing symptoms alone. The difficulty when dealing with a potentially dangerous viral outbreak is amplified when those outbreaks are frequent and widespread. The SARS coronavirus spread widely in 2003, and a much larger H1N1 swine flu pandemic followed in 2009. More recently, Ebola has appeared in Africa. MERS has been found in people in the Middle East, and the H5N1 bird flu that has killed many birds has proven able to spread from birds to people.

It may be possible to use DNA sequencing to identify viruses or their specific strains and even to help develop vaccines. However, viruses are capable of rapid mutation and may even benefit from having changing genetic sequences by being better able to evade the host's immune system. For example, new flu vaccines are recommended each year because the influenza virus mutates so rapidly. Moreover, we now understand that a virus may exist in a host as a "quasispecies"—a group of a very large number of closely-related viral genomes that is suited to evade immune destruction by virtue of the inclusion of many random but novel variants any one of which may survive an immune response. Thus when a person is infected with a virus, not only might the virus represent a significant public health threat, the nature of its rapidly mutating genome can make it very difficult to identify and treat.

SUMMARY

The invention provides systems and methods for analyzing viruses by representing viral genetic diversity with a reference graph, such as a directed acyclic graph (DAG), which allows genetic sequencing technology to detect rare variations and represent otherwise difficult-to-document diversity within a sample. Additionally, a host-specific sequence DAG can be used to effectively segregate viral nucleic acid sequence reads from host sequence reads when a sample from a host is subject to sequencing. Known viral genomes can be represented using a viral reference DAG and the viral sequence reads from the sample can be compared to the viral reference DAG to identify viral species or strains from which the reads were derived. Where the viral sequence reads indicate great genetic diversity in the virus that was infecting the host, those reads can be assembled into a DAG that itself properly represents that diversity, instead of requiring the output of sequencing to be artificially collapsed into one or more linear sequences that are then taken to be "the genome" of the infecting virus. By providing the sequencing results as a DAG, the genetic diversity of the infecting agent can be properly represented and, in-fact, a viral quasispecies can fairly be described by the output.

Since the known viral reference genomes can be represented as a viral reference DAG, mapping the viral sequence reads to a reference is not limited by the implicit assumptions inherent in comparing linear sequences to a series of linear entries in a database. In fact, the viral reference DAG may be populated by retrieving entries from a database and transforming those sequences into a DAG, which itself represents inferences of relatedness among viral strains and also avoids data redundancy. Not only does a DAG avoid data redundancy, implementation of a DAG allows the reference genomes to be queried very rapidly as the reference genomes are embodied as paths through the DAG and paths through a DAG can be traversed via index-free adjacency much more rapidly than other traditional flat-file data structures can be queried. Due to the ways in which a genomic reference DAG avoids redundancy and inherently supports very rapid traversals, use of a DAG for mapping sequence reads allows a much greater quantity of reference data to be queried, and much faster, than other approaches such as BLAST comparisons to GenBank. Those same speed and capacity benefits obtain using a human reference DAG. Where sequence reads are obtained from a sample from an infected human, comparison to a human DAG allows host-derived reads to be discarded, ensuring that the reads that go into viral discovery and analysis are all the true viral sequence reads. Not only is a reference DAG as a data structure a very effective tool for read-mapping—i.e., discovering relationships between reads from a sample and reference genomic information—a DAG also proves to be an excellent way to represent genetic diversity found in the sample. As a data structure, it allows many closely-related genomes to be stored in a compact format that represents homology among all segments of all the represented sequences. A reference DAG is also suited to be presented visually to effectively demonstrate the genetic diversity present. For those reasons, a DAG is particularly well-suited to represent a quasispecies. While a sequencing instrument generates reads from a sample, the system can transform those reads into an article, the DAG, that represents all of the variations found within the sample and that DAG can be used to store or depict all of that variation, and thus can be used to represent a quasispecies.

In certain aspects, the invention provides a method for analyzing a virus. The method includes obtaining a sequence from a sample containing viral nucleic acid and converting—using a processor coupled to a tangible memory subsystem—the sequence into an alignment with one of a plurality of known viral sequences stored as a reference directed acyclic graph (DAG) comprising objects in the tangible memory subsystem. In the viral DAG, segments of the known viral sequences that match each other when aligned are each represented by a single object in the reference DAG. An identity of a virus for the one of the plurality of known viral sequences is retrieved and a report is provided that includes the identity of the virus.

The method may include (e.g., prior to the aligning step) obtaining the plurality of known viral sequences from an online sequence database, finding and deleting redundancies among homologous portions of the known viral sequences while leaving the segments of the known viral sequences that match each other when aligned, and creating one of the objects in the tangible memory subsystem for each of the segments, thereby transforming the known viral sequences from the online sequence database into the reference DAG.

In some embodiments, the report includes a list of viral species or strains determined by analyzing sequences from the sample, and the report further quantifies an amount of each viral species or strain present in the viral nucleic acid. In certain embodiments, the known viral sequences are of the same species as the viral nucleic acid, and methods of the invention are used to characterize a quasispecies of the virus in the sample. The report may include a list of strains of the virus, a graphic representation of a DAG of aligned sequence reads from the sample, or both.

Methods of the invention may be used to identify tumor-associated virus genes, e.g., by obtaining sequence reads from genomic nucleic acid from a healthy cell of a subject, aligning the sequence reads to a human reference DAG, and creating a subject-specific reference DAG that includes a plurality of variants identified in the aligning step. Disease-type sequence reads may be obtained from a diseased cell such as from a tumor of the subject and aligning them to the subject-specific reference DAG. Any disease-type sequence reads that do not align and disease-type sequence reads that contain variants relative to the subject-specific reference DAG are considered candidate reads. The candidate reads are aligned to the reference DAG representing known viral sequences. A report can be provided that includes the identities of one or more viruses identified by aligning the candidate reads to the reference DAG representing known viral sequences.

In some embodiments, a plurality of sequence reads are obtained from a sample, e.g., as the output of a nucleic acid sequencing instrument. Methods of the invention may include sequencing nucleic acid from the sample using the sequencing instrument.

In some embodiments, the objects of the reference DAG include pointers to adjacent ones of the objects such that the objects are linked into paths to represent the plurality of known viral sequences, wherein each pointer identifies a physical location in the memory subsystem at which the adjacent object is stored. Objects of the reference DAG may include vertex objects connected by edge objects and an adjacency list for each vertex object and edge object, such that the adjacency list for a vertex object or edge object lists the edge objects or vertex objects to which that vertex object or edge object is adjacent. Each entry in an adjacency list may be a pointer to the adjacent vertex object or edge object, such that each pointer identifies a physical location in the memory subsystem at which the adjacent object is stored. In some embodiments, the reference DAG uses index-free adjacency to link the objects into paths to represent the plurality of known viral sequences.

Converting the sequence into the alignment may be done by using the processor to perform a multi-dimensional look-back operation to find a highest-scoring trace through a multi-dimensional matrix.

Aspects of the invention provide a system for analyzing a virus. The system includes a processor coupled to a tangible memory subsystem and is operable to obtain a sequence from a sample containing viral nucleic acid and convert the sequence into an alignment with one of a plurality of known viral sequences stored as a reference directed acyclic graph (DAG) that includes objects in the tangible memory subsystem. In the reference DAG, segments of the known viral sequences that match each other when aligned are each represented by a single object in the reference DAG. The system can retrieve an identity of a virus for the one of the plurality of known viral sequences and provide, via an input/output device coupled to the processor, a report that includes the identity of the virus. Preferably, the system can be used to obtain the plurality of known viral sequences from an online sequence database, find and delete redundancies among homologous portions of the known viral sequences thus leaving the segments of the known viral sequences that match each other when aligned, and create one of the objects in the tangible memory subsystem for each of the segments, thereby transforming the known viral sequences from the online sequence database into the reference DAG. The report produced by the system may include a list of viral species or strains determined by analyzing sequences from the sample, and the report further quantifies an amount of each viral species or strain present in the viral nucleic acid.

The system may be operated to characterize a quasispecies in a sample, e.g., using a viral reference DAG in which the known viral sequences are of the same species as the viral nucleic acid. The system may produce a report that includes a list of strains of the virus and a graphic representation of a DAG of aligned sequence reads from the sample to illustrate the quasispecies.

In some embodiments, the system is operable to obtain sequence reads from genomic nucleic acid from a healthy cell of a subject, align the sequence reads to a human reference DAG, and create a subject-specific reference DAG that includes a plurality of variants identified in the aligning step. The system obtains disease sequence reads from a diseased cell of the subject and aligns them to the subject-specific reference DAG. Disease sequence reads that do not align and disease sequence reads that contain variants relative to the subject-specific reference DAG are considered candidate reads. The system aligns the candidate reads to the reference DAG representing known viral sequences. The system produces a report that includes the identities of one or more viruses identified by aligning the candidate reads to the reference DAG representing known viral sequences.

In certain embodiments, the system includes a nucleic acid sequencing instrument and the system is operable to obtain a plurality of sequence reads from the sample by sequencing nucleic acid in the sample.

In a preferred embodiment, the objects of the reference DAG include pointers to adjacent ones of the objects such that the objects are linked into paths to represent the plurality of known viral sequences, wherein each pointer identifies a physical location in the memory subsystem at which the adjacent object is stored. Objects of the reference DAG may include vertex objects connected by edge objects and an adjacency list for each vertex object and edge object, such that the adjacency list for a vertex object or edge object lists the edge objects or vertex objects to which that vertex object or edge object is adjacent. Each entry in an adjacency list may be a pointer to the adjacent vertex object or edge object and each pointer may identify a physical location in the memory subsystem at which the adjacent object is stored. The reference DAG may use index-free adjacency to link the objects into paths to represent the plurality of known viral sequences. The processor can convert the sequence into the alignment by performing a multi-dimensional look-back operation to find a highest-scoring trace through a multi-dimensional matrix.

BRIEF DESCRIPTION OF THE DRAWINGS

FIG. 9 shows the matrices that represent the comparison.

DETAILED DESCRIPTION

Viral typing—determining the type or subtype of a virus—is an important part of infection control and public health. Next-generation sequencing (NGS) techniques may be applied to the identification of viral infections via viral typing. See e.g., Prachayangprecha et al., 2014, Exploring the potential of next-generation sequencing in detection of respiratory viruses, J Clin Microbiol 52(10):3722-3730, incorporated by reference. Existing techniques rely on de novo assembly of reads into contigs followed by a search using the contigs as inputs of databases of known virus genomes for typing. Systems and methods of the invention represent the known virus genomes using a viral reference DAG and allow (i) read assembly and (ii) comparison to known reference sequences to be collapsed into a single operation. Uniting those steps provides for increased accuracy as information about known viruses is taken advantage of in the course of assembly.

Methods of the invention are particularly well-suited to virology for several reasons. First, the natural background diversity in the human virome and the difficulty of isolating viral nucleic acids from host nucleic acids means that reads from a sample will generally represent host and viral genetic information, not just the viral. Additionally, many viruses are best characterized as existing in quasispecies, in which there is a high degree of genetic variability within the host as well as a high rate of mutation. A viral quasispecies is a group of viruses in a mutagenic environment, related by a similar mutations. Theoretically, a viral quasispecies that occupies a low but large, flat region in the fitness landscape will outcompete a quasispecies located at a higher but narrower fitness peak. See Andino & Domingo, 2015, viral quasispecies, Virology 479-480:46-51 and Presloid & Novella, 2015, RNA Viruses and RNAi: Quasispecies implications for viral escape, Viruses 7(6):3226-40, each incorporated by reference. The quasispecies model is applicable to RNA viruses because they have high mutation rates and extremely large populations—conditions thought to favor quasispecies. One implication of a virus being present as a quasispecies, and quasispecies having adaptive advantages, is that a treatment (e.g., an antibody or a drug) that effectively inhibits viruses with specific sequences may not exhibit any practical effect on an infection by a quasispecies. Relevant detail may be found in Capobianchi et al., 2012, Next-generation sequencing technology in clinical virology, Clin Microbiol & Infect 19:15-22, incorporated by reference.

A quasi-species is naturally best represented by DAGs, and alignment to a robust DAG is more likely to catch mutations present in low proportions to the overall viral population, any or many of which mutations may turn out to be significant to drug resistance.

Embodiments of the invention are provided for the identification of a species of a virus.

Figure 1:
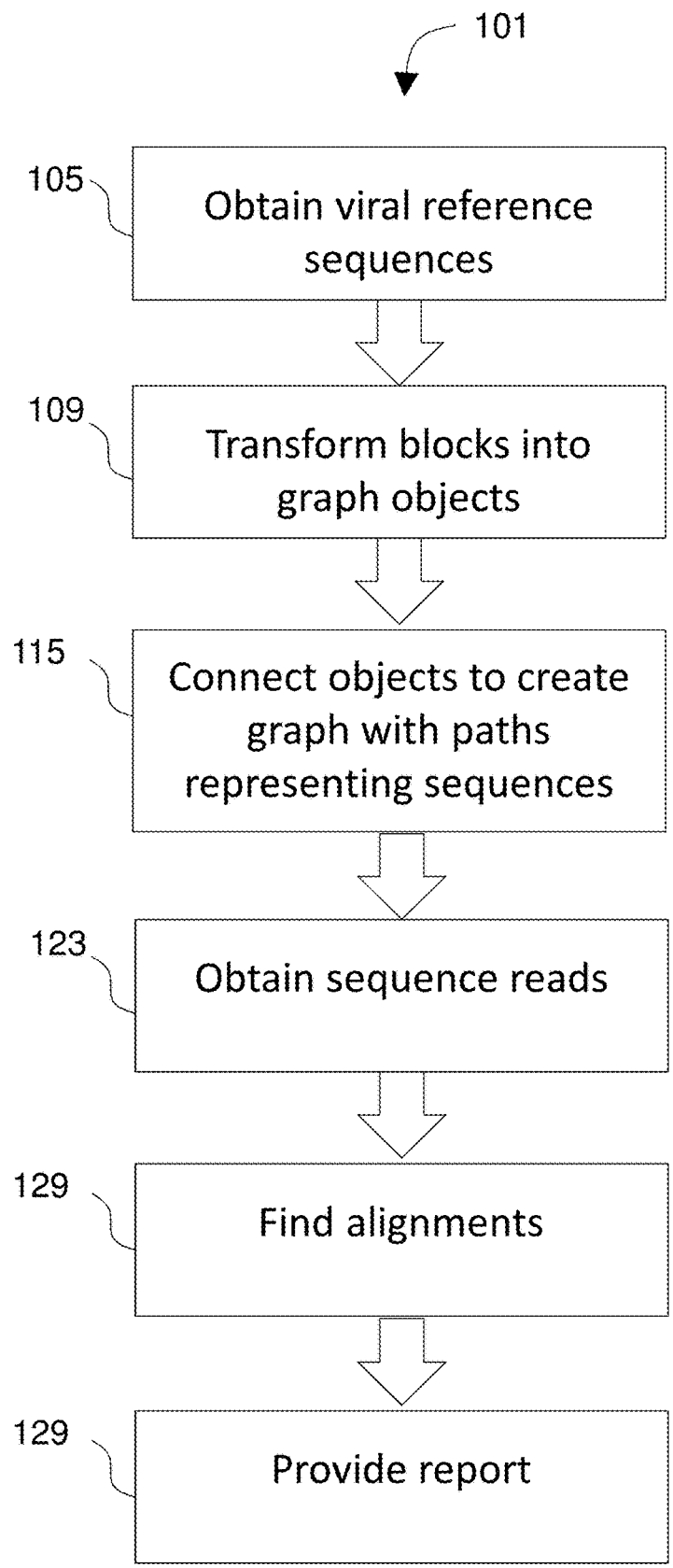
FIG. 1 diagrams a method for analyzing a viral sequence from an organism.

FIG. 1 diagrams a method 101 for analyzing a viral sequence from an organism. At step 105 a plurality of reference viral sequences are obtained. Portions of the sequences that match each other when aligned are identified as blocks that are transformed 109 into objects that are stored in a tangible memory device. The objects are connected 115 to create paths such that there is a path for each of the original viral sequences. This creates a new article, a viral reference DAG comprising objects stored in the tangible memory device.

In certain embodiments, the directed graph may be created by associating an initial object with a viral reference genome. Known variations from the reference genome previously observed across a population or known quasi-species, such as single nucleotide polymorphisms, small insertions and deletions (indels), and larger structural variants, may be associated with additional objects. The object representing the viral reference genome may then be divided into multiple objects at positions in which the known variations occur, and the plurality of objects are then connected to create paths such that there is a path for each known variation. A plurality of viral reference genomes and known variations may be accessed via the NCBI Viral Genomes Database (www.ncbi.nlm.nih.gov/genome/viruses/), a resource that provides viral and viroid genome sequence data, for example.

Method 101 preferably further includes obtaining 123 sequence reads from a sample from a subject. Sequence reads can be obtained from a nucleic acid sequencing instrument. Optionally, a subject-specific reference DAG may be used to remove non-viral reads, leaving viral reads for the subsequent identification. A processor coupled to the tangible memory device is used to find 129 alignments between the viral sequence reads and the paths through the viral reference DAG. A report is provided 129 that identifies a one or more of the viral sequences that aligned to the sequence reads. Specifically, the report may characterize one or a plurality of viruses in the organism, identify significant mutations or other genetic features in the virus, describe a quasispecies, or otherwise describe the organism and its virome.

Figure 2:
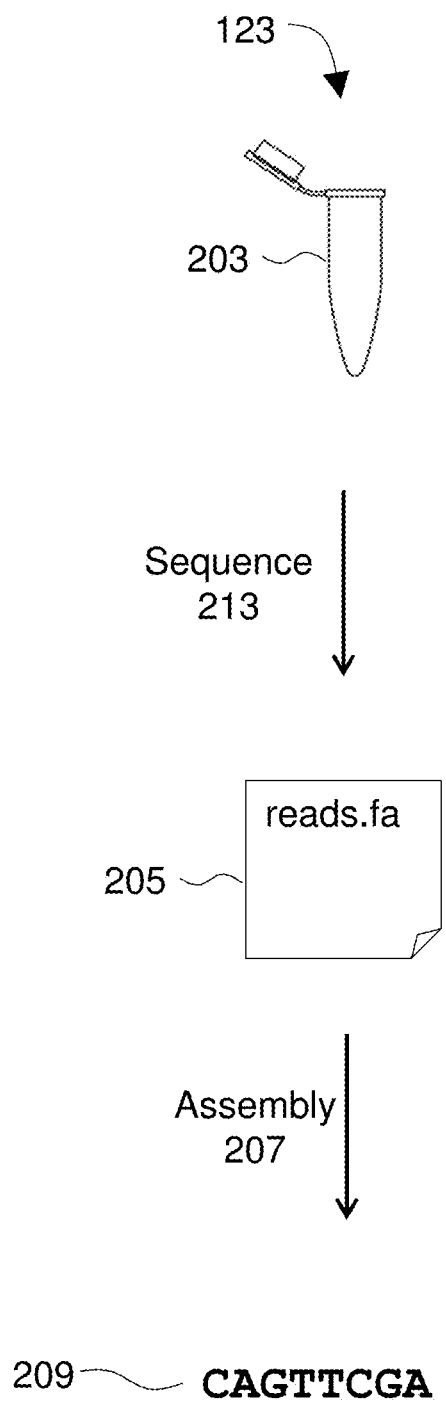
FIG. 2 illustrates obtaining sequence reads from a sample.

FIG. 2 illustrates obtaining 123 sequence reads 205 from a sample 203. As a preliminary step (not depicted), host nucleic acid may be depleted and/or viral nucleic acid enriched. For example, a sample may be digested with modification specific nucleases such as methylation-specific endonucleases as described in Oyola et al., 2013, Efficient depletion of host DNA contamination in malaria clinical sequencing, J Clin Microbiol 51(3):745-51, incorporated by reference. To enrich viral particles, strategies may also include removal of host ribosomal RNA (He et al., 2010, Validation of two ribosomal RNA removal methods for microbial metatranscriptomics. Nat Methods 7:807-812, incorporated by reference), and/or removal of the most abundant host sequences by duplex-specific nuclease (DSN) normalization (Shagina et al., 2010, Normalization of genomic DNA using duplex specific nuclease, Biotechniques 48:455-459, incorporated by reference). Another approach includes using biotinylated probes to enrich NGS libraries for sequences corresponding to pathogens as described, e.g., in Gnirke et al., 2009, Solution hybrid selection with ultra-long oligonucleotides for massively parallel targeted sequencing. Nat Biotechnol 2009, 27:182-189, incorporated by reference. After an optional enrichment step, the sample 203 includes viral nucleic acid from a virus in a subject.

In certain embodiments, sequence reads are obtained by performing sequencing 213 on a sample 203 from a subject (however in some embodiments, sequence reads are obtained when a read file is transferred into a system of the invention). Sequencing may be by any method and sequencing instrument known in the art. See, generally, Quail, et al., 2012, A tale of three next generation sequencing platforms: comparison of Ion Torrent, Pacific Biosciences and Illumina MiSeq sequencers, BMC Genomics 13:341. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing.

A sequencing technique that can be used includes, for example, use of sequencing-by-synthesis systems and sequencing instruments sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, each incorporated by reference. 454 sequencing involves two steps. First, DNA is sheared into blunt-end fragments attached to capture beads and then amplified in droplets. Second, pyrosequencing is performed on each DNA fragment in parallel. Addition of nucleotides generates a light signal that is recorded by a CCD camera in a sequencing instrument.

Another sequencing technique and instrument that can be used is SOLiD technology by Applied Biosystems from Life Technologies Corporation (Carlsbad, Calif.). In SOLiD sequencing, genomic DNA is sheared into fragments, and adaptors are attached to generate a fragment library. Clonal bead populations are prepared in microreactors containing beads, primers, template, and PCR components. Following PCR, the templates are denatured and enriched and the sequence is determined by a process that includes sequential hybridization and ligation of fluorescently labeled oligonucleotides.

Another example of a DNA sequencing technique and instrument that can be used is ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pubs. 2009/0026082, 2009/0127589, 2010/0035252, 2010/0137143, 2010/0188073, 2010/0197507, 2010/0282617, 2010/0300559, 2010/0300895, 2010/0301398, and 2010/0304982, each incorporated by reference. DNA is fragmented and given amplification and sequencing adapter oligos. The fragments can be attached to a surface. Addition of one or more nucleotides releases a proton (H+), which signal is detected and recorded in a sequencing instrument.

Another example of a sequencing technology that can be used is Illumina sequencing. Illumina sequencing is based on the amplification of DNA on a solid surface using fold-back PCR and anchored primers. Genomic DNA is fragmented and attached to the surface of flow cell channels. Four fluorophore-labeled, reversibly terminating nucleotides are used to perform sequential sequencing. After nucleotide incorporation, a laser is used to excite the fluorophores, and an image is captured and the identity of the first base is recorded. Sequencing according to this technology is described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

Other examples of a sequencing technology that can be used include the single molecule, real-time (SMRT) technology of Pacific Biosciences (Menlo Park, Calif.) and nanopore sequencing as described in Soni and Meller, 2007 Clin Chem 53:1996-2001.

As shown in FIG. 2, sequencing 213 generates a plurality of reads 205. Reads according to the invention generally include sequences of nucleotide data anywhere from tens to thousands of bases in length. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 123 in a format such as FASTA, FASTQ, or similar.

Figure 3:
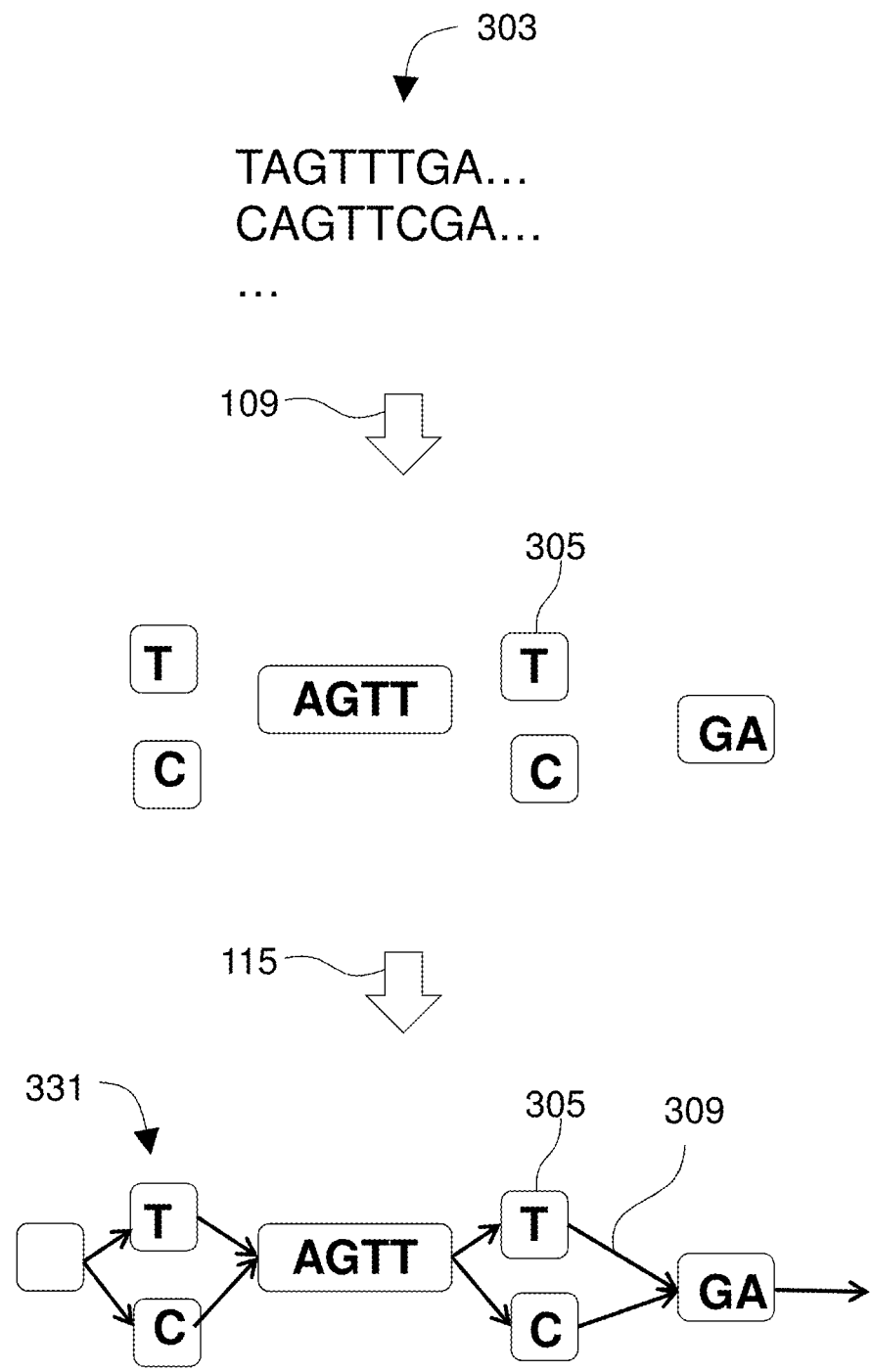
FIG. 3 illustrates obtaining viral reference sequences and transforming the reference sequences into a viral reference DAG.

Sequence reads 205 may be directly aligned to a graph, such as the graph 331 of FIG. 3. In some embodiments, the sequence reads 205 are assembled 207 to provide a contig or consensus sequence 209, which contig or consensus sequence may be used in finding alignments to the viral reference DAG 331. Sequence assembly 207 may include any suitable methods known in the art including de novo assembly, reference-guided assembly, others, or combinations thereof. In a preferred embodiment, sequence reads are assembled 207 using graph-based alignment methods. See, e.g., U.S. Pub. 2015/0057946 and U.S. Pub. 2015/0056613, both incorporated by reference. Embodiments of a graph and its use are discussed in greater detail below. The result of assembly 207 is a sequence 209 representing the corresponding portion of a viral nucleic acid. The contig or consensus sequence 209 or one or more of the sequence reads 205 may then be mapped to a viral reference DAG to find an alignment with an optimal score.

The invention provides methods for creating a viral reference DAG.

FIG. 3 illustrates obtaining viral reference sequences 303 and transforming 109 the reference sequences 303 into a viral reference DAG 331 that includes vertex objects 305 and edge objects 309. The viral sequences 303 may be retrieved from a database. For example, a computer system may be used to execute instructions (e.g., using SQL, Perl, Python, or similar suitable scripting and query platform) to retrieve viral genome sequence data from the NCBI virus genomes database as described in Brister et al., 2015, NCBI viral genomes resource, Nucleic Acids Research 43 (Database issue):D571-7, incorporated by reference. That resource catalogs all complete viral genomes deposited in the International Nucleotide Sequence Database Collaboration (INSDC) databases and creates RefSeq records for each viral species. Each RefSeq is derived from an INSDC sequence record, but may include additional annotation and/or other information. Accessions for RefSeq genome records include the prefix 'NC_', allowing them to be easily differentiated from INSDC records. For example, the RefSeq genome record for Enterobacteria phage T4 has the accession NC_000866 but was derived from the INSDC record AF158101. Typically, the first genome submitted for a particular species is selected as a RefSeq, and once a RefSeq is created, other validated genomes for that species are indexed as 'genome neighbors'. As such, the viral RefSeq data model is taxonomy centric and all RefSeq records and genome neighbors are indexed at the species level. This model requires both the demarcation of individual viral species and the grouping of genome sequences into defined species. Users can download accession list of all viral and viroid genomes (RefSeq and genome neighbors) and the complete viral and viroid RefSeq dataset. That resource includes viral and viroid genome browsers. Tables list all viral and viroid species represented by a reference sequence and include links to genome neighbor sequences. Users can navigate to specific taxonomic groups and sort the table by viral host type. Once a dataset has been defined by taxonomy and host types, users can download the resultant table, the list of RefSeq accessions in the table, or a list that includes RefSeq and genome neighbor accessions as well as taxonomy and viral host information. By defining a search term and sending it using, e.g., Perl or Python, a local computer can obtain the sequences 303 from an online database.

Each of the sequences 303 are aligned to one another, preferably by being aligned to an object containing information from each other sequence. In a preferred embodiment, the sequences are aligned by the process of building them into the viral reference DAG using the modified multi-dimensional Smith Waterman operation defined herein. In some embodiments, it may be useful or convenient to perform a multiple sequence alignment among sequences 303, e.g., using Clustal. Multiple sequence alignment is discussed in more detail below. Portions of the sequences that match each other when aligned are identified as blocks and those blocks are transformed 109 into objects 205 that are stored in a tangible memory device.

In the fragments of sequence represented in FIG. 3, it can be seen that bases 2-5 of the first sequence (TAGTTTGA) align to, and match, bases 2-5 of the second sequence (CAGTTCGA). Thus those segments of those two sequences are identified as a block and systems of the invention create an object 305 to represent that AGTT string. It is noted that this object could potentially be stored using one byte of information. For example, if A=00, C=01, G=10, and T=11, then this block contains 00101111 (one byte). Where the original sequences 303 contain thousands of viral genomes, the described methods provide a considerable improvement to the operation of the computer system in comparison to a prior art method that stores an entire multiple sequence alignment.

The objects 305 are connected 115 to create paths such that there is a path for each of the original viral sequences. The paths are directed and preferably in the sense that the direction of each path corresponds to the 5' to 3' directionality of the viral nucleic acid. However, it is noted that it may be convenient or desirable to represent a virus in a 3' to 5' direction and that doing so does not leave the scope of the invention. The connections creating the paths can themselves be implemented as objects so that the blocks are represented by vertex objects 305 and the connections are represented by edge objects 309. Thus the directed graph comprises vertex and edge objects stored in the tangible memory device. The directed graph 331 represents the plurality of viral sequences 303 in that each one of the original sequences can be retrieved by reading a path in the direction of that path. However, the directed graph 331 is a different article that the original sequences 303, at least in that portions of the sequences that match each other when aligned have been transformed into single objects 303. Thus if the original article includes 90,000 full viral genomes in which a coat protein gene segment is perfectly conserved for a span of 12,000 bp across all of the genomes, then over 1 billion characters of information from the original article are transformed into a single object that can use less than 3 KB on disk.

By such means, the known viral genomes are transformed into a viral reference DAG. Where a DAG is used to represent homologous sequences, it may be convenient to have one or more source nodes correspond to the 5' end of those sequences and one or more sink nodes correspond to the 3' end. In certain embodiments, the sequence data is stored in the edge objects 309. This may be useful, e.g., where the 5'-most nucleotide is not conserved across the plurality of linear sequences but a finite DAG is desired. Thus the source node object 305 does not store any sequence data and each edge object 309 includes relevant sequence data.

It may be possible to store the sequence strings within either the vertex objects 305 or the edge objects 309 (node and vertex are used synonymously). As used herein, node object 305 and edge object 309 refer to an object created using a computer system.

Figure 4:
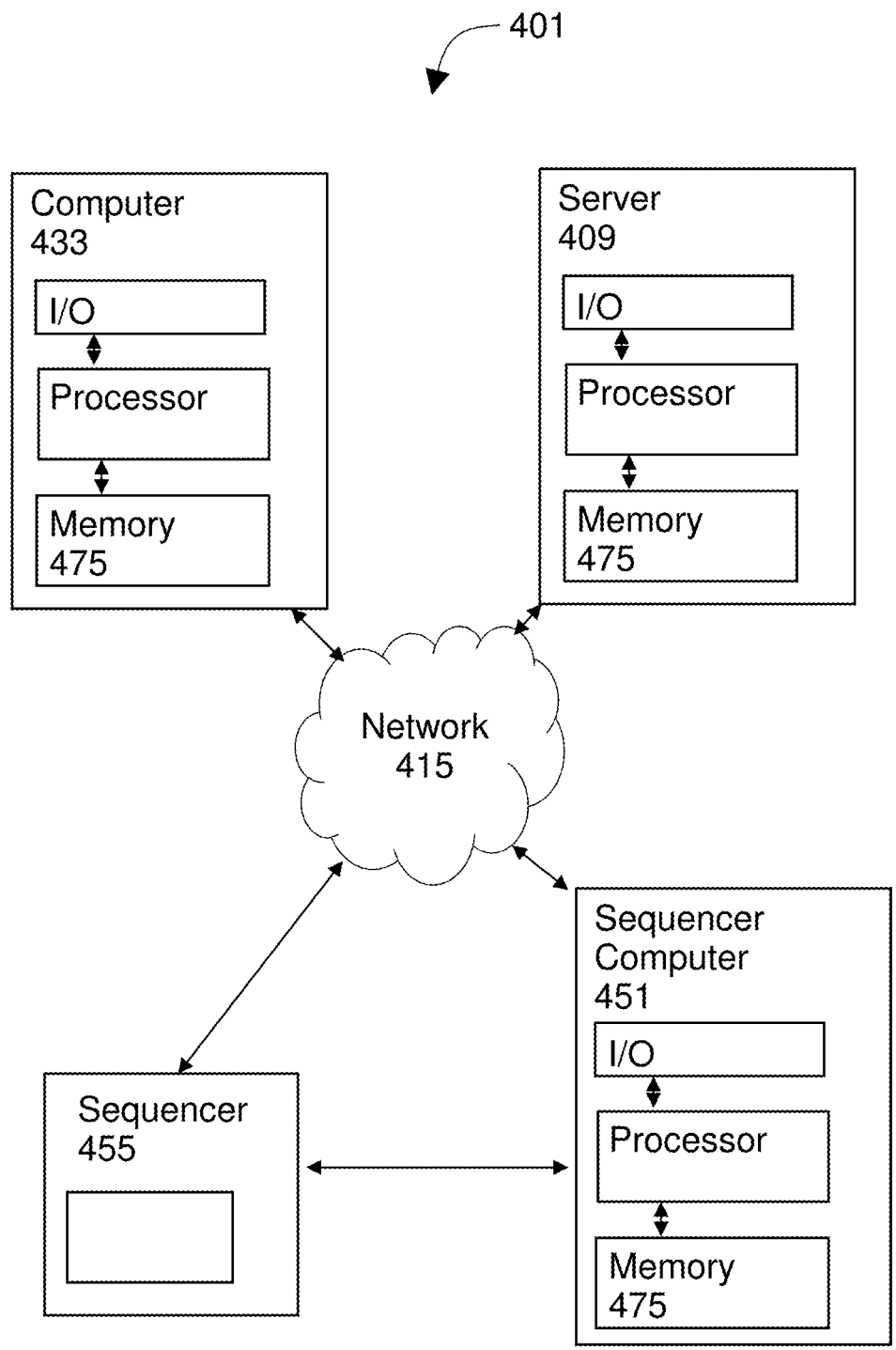
FIG. 4 illustrates a computer system for performing methods of the invention.

FIG. 4 illustrates a computer system 401 suitable for performing methods of the invention. The system 401 includes at least one computer 433. Optionally, the system 401 may further include one or more of a server computer 409 and a sequencer 455, which may be coupled to a sequencer computer 451. Each computer in the system 401 includes a processor coupled to a memory device and at least one input/output device. Thus the system 401 includes at least one processor coupled to a memory subsystem (e.g., a memory device or collection of memory devices 475). Using those mechanical components, the system 401 is operable to obtain a sequence generated by sequencing nucleic acid from a genome of a patient. The system uses the processor to transform the sequence 303 into the viral reference DAG 331.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The memory subsystem 475 contains one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 401 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Preferably the viral reference DAG is stored in the memory subsystem using adjacency techniques, which may include pointers to identify a physical location in the memory subsystem 475 where each vertex is stored. In a preferred embodiment, the graph is stored in the memory subsystem 475 using adjacency lists. In some embodiments, there is an adjacency list for each vertex. For discussion of implementations see 'Chapter 4, Graphs' at pages 515-693 of Sedgewick and Wayne, 2011, Algorithms, 4th Ed., Pearson Education, Inc., Upper Saddle River N.J., 955 pages, the contents of which are incorporated by reference and within which pages 524-527 illustrate adjacency lists.

Figure 5:
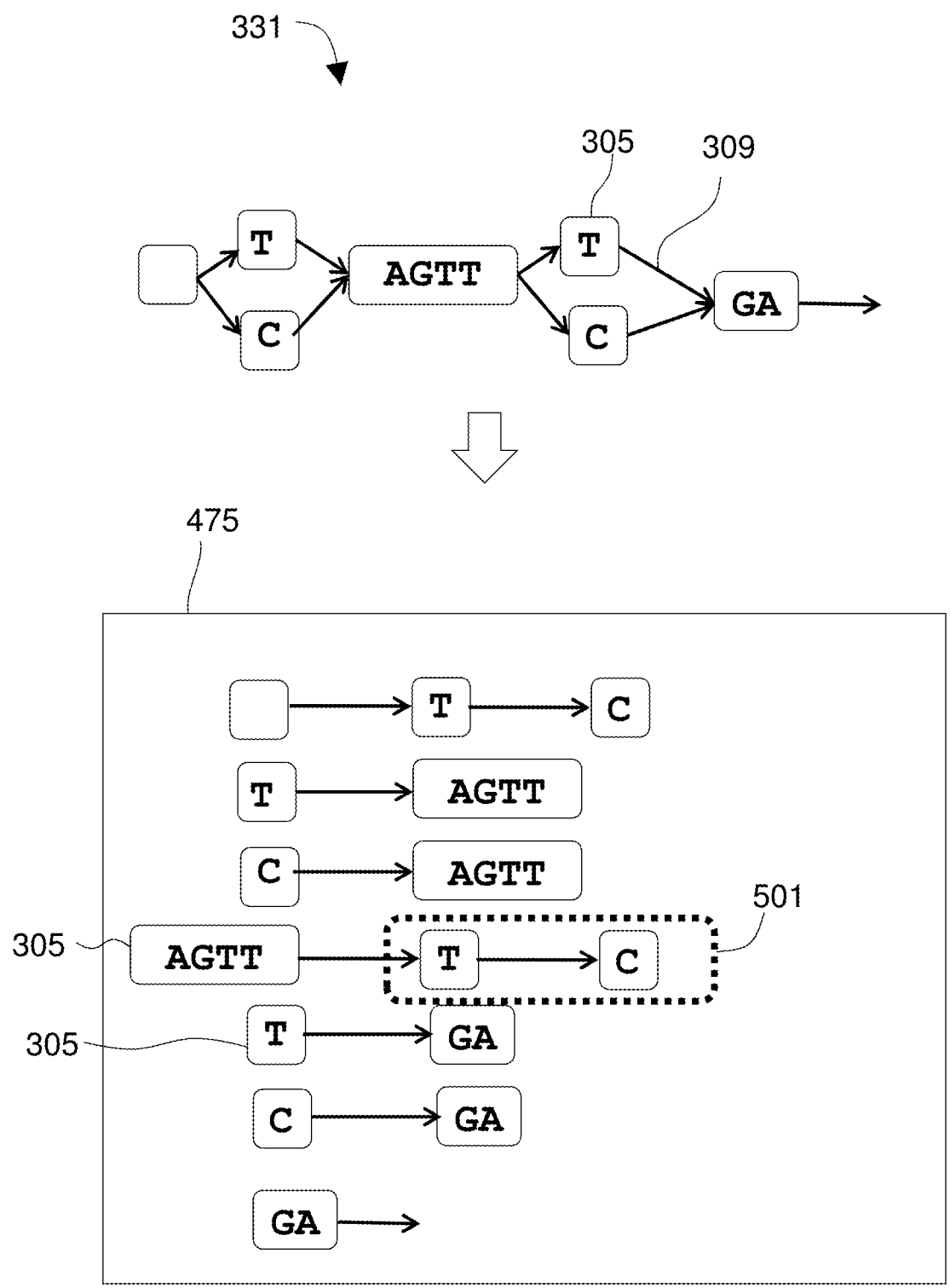
FIG. 5 shows the use of an adjacency list for each vertex in a DAG.

FIG. 5 shows the use of an adjacency list 501 for each vertex 305. The system 401 uses a processor to create a graph 331 that includes vertex objects 305 and edge objects 309 through the use of adjacency, i.e., adjacency lists or index free adjacency. Thus, the processor may create the viral reference DAG 331 using index-free adjacency wherein a vertex 305 includes a pointer to another vertex 305 to which it is connected and the pointer identifies a physical location in on a memory device 475 where the connected vertex is stored. The viral reference DAG 331 may be implemented using adjacency lists such that each vertex or edge stores a list of such objects that it is adjacent to. Each adjacency list comprises pointers to specific physical locations within a memory device for the adjacent objects.

In the top part of FIG. 5, the viral reference DAG 331 is illustrated in a cartoon-like visual-friendly format. The viral reference DAG 331 will typically be stored on a physical device of memory subsystem 475 in a fashion that provide for very rapid traversals. In that sense, the bottom portion of FIG. 5 is not cartoon-like and represents that objects are stored at specific physical locations on a tangible part of the memory subsystem 475. Each node 305 is stored at a physical location, the location of which is referenced by a pointer in any adjacency list 501 that references that node. Each node 305 has an adjacency list 501 that includes every adjacent node in the viral reference DAG 331. The entries in the list 501 are pointers to the adjacent nodes.

In certain embodiments, there is an adjacency list for each vertex and edge and the adjacency list for a vertex or edge lists the edges or vertices to which that vertex or edge is adjacent.

Figure 6:
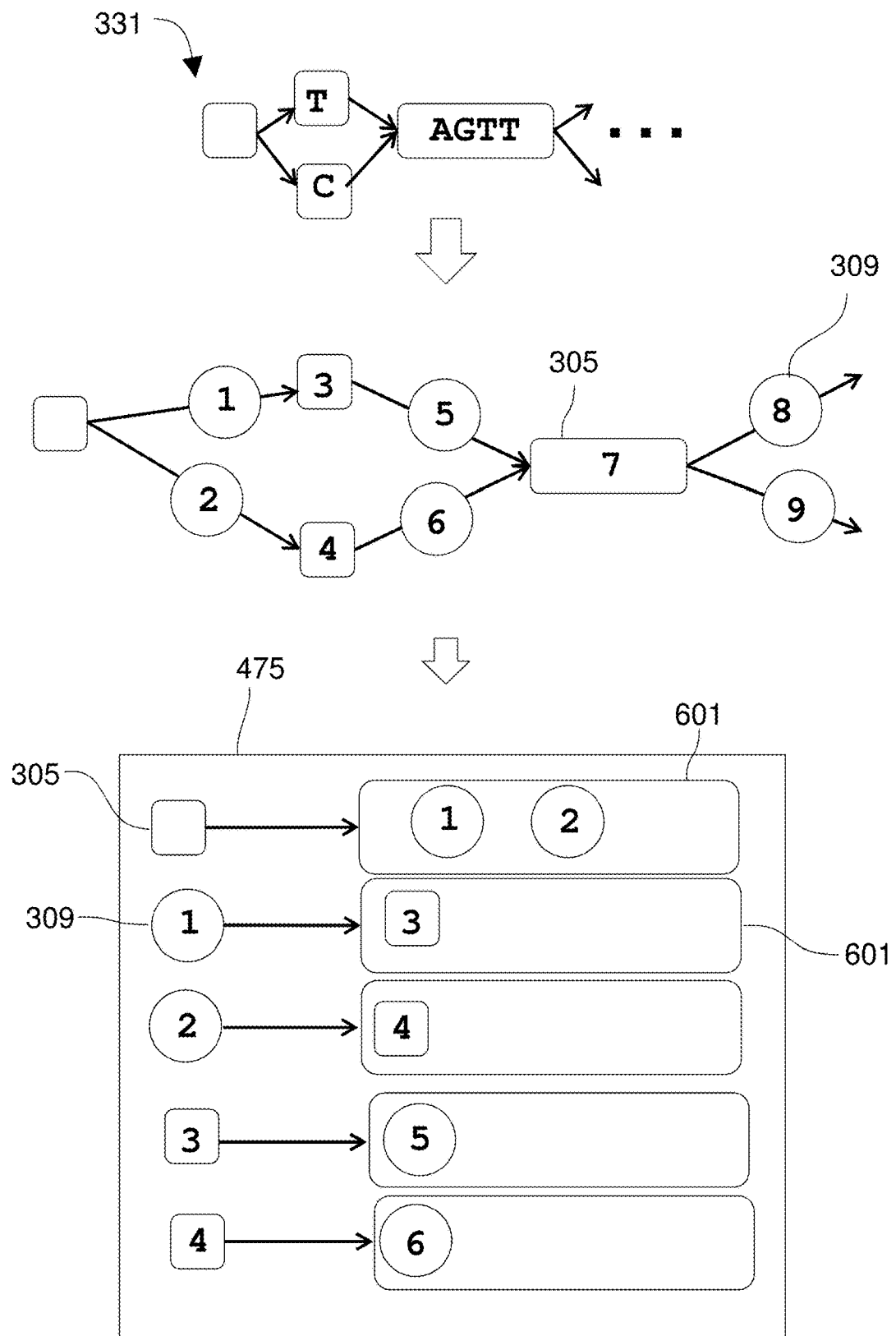
FIG. 6 shows the use of an adjacency list for each vertex and edge in a DAG.

FIG. 6 shows the use of an adjacency list 601 for each vertex 305 and edge 309. As shown in FIG. 6, system 401 creates the viral reference DAG 331 using an adjacency list 601 for each vertex and edge, wherein the adjacency list 601 for a vertex 305 or edge 309 lists the edges or vertices to which that vertex or edge is adjacent. Each entry in adjacency list 601 is a pointer to the adjacent vertex or edge.

Preferably, each pointer identifies a physical location in the memory subsystem at which the adjacent object is stored. In the preferred embodiments, the pointer or native pointer is manipulatable as a memory address in that it points to a physical location on the memory and permits access to the intended data by means of pointer dereference. That is, a pointer is a reference to a datum stored somewhere in memory; to obtain that datum is to dereference the pointer. The feature that separates pointers from other kinds of reference is that a pointer's value is interpreted as a memory address, at a low-level or hardware level. The speed and efficiency of the described graph genome engine allows a sequence to be queried against a large-scale genomic reference graph 331 representing millions or billions of bases, using a computer system 401. Such a graph representation provides means for fast random access, modification, and data retrieval.

In some embodiments, fast random access is supported and graph object storage are implemented with index-free adjacency in that every element contains a direct pointer to its adjacent elements (e.g., as described in U.S. Pub. 2014/0280360 and U.S. Pub. 2014/0278590, each incorporated by reference), which obviates the need for index look-ups, allowing traversals (e.g., as done in the modified SW alignment operation described herein) to be very rapid. Index-free adjacency is another example of low-level, or hardware-level, memory referencing for data retrieval (as required in alignment and as particularly pays off in terms of speed gains in the modified, multi-dimensional Smith-Waterman alignment described below). Specifically, index-free adjacency can be implemented such that the pointers contained within elements are references to a physical location in memory.

Since a technological implementation that uses physical memory addressing such as native pointers can access and use data in such a lightweight fashion without the requirement of separate index tables or other intervening lookup steps, the capabilities of a given computer, e.g., any modern consumer-grade desktop computer, are extended to allow for full operation of a genomic-scale graph (i.e., a graph 331 that represents all loci in a substantial portion of the viral genome). Thus storing graph elements (e.g., nodes and edges) using a library of objects with native pointers or other implementation that provides index-free adjacency actually improves the ability of the technology to provide storage, retrieval, and alignment for genomic information since it uses the physical memory of a computer in a particular way.

While no specific format is required for storage of a graph, FIGS. 5 and 6 are presented to illustrate useful formats. With reference back to FIG. 1, it is noted that methods of the invention use the stored graph with sequence reads that are obtained from a subject. In some embodiments, sequence reads are obtained as an electronic article, e.g., uploaded, emailed, or FTP transferred from a lab to system 401. In certain embodiments, sequence reads are obtained by sequencing.

Methods may include using a subject-specific reference DAG as an optional preliminary step and then using a viral reference DAG for the analysis of sequence reads. A subject-specific reference DAG may be used to remove host-derived reads where sequence reads are obtained from a mixed sample.

Figure 7:
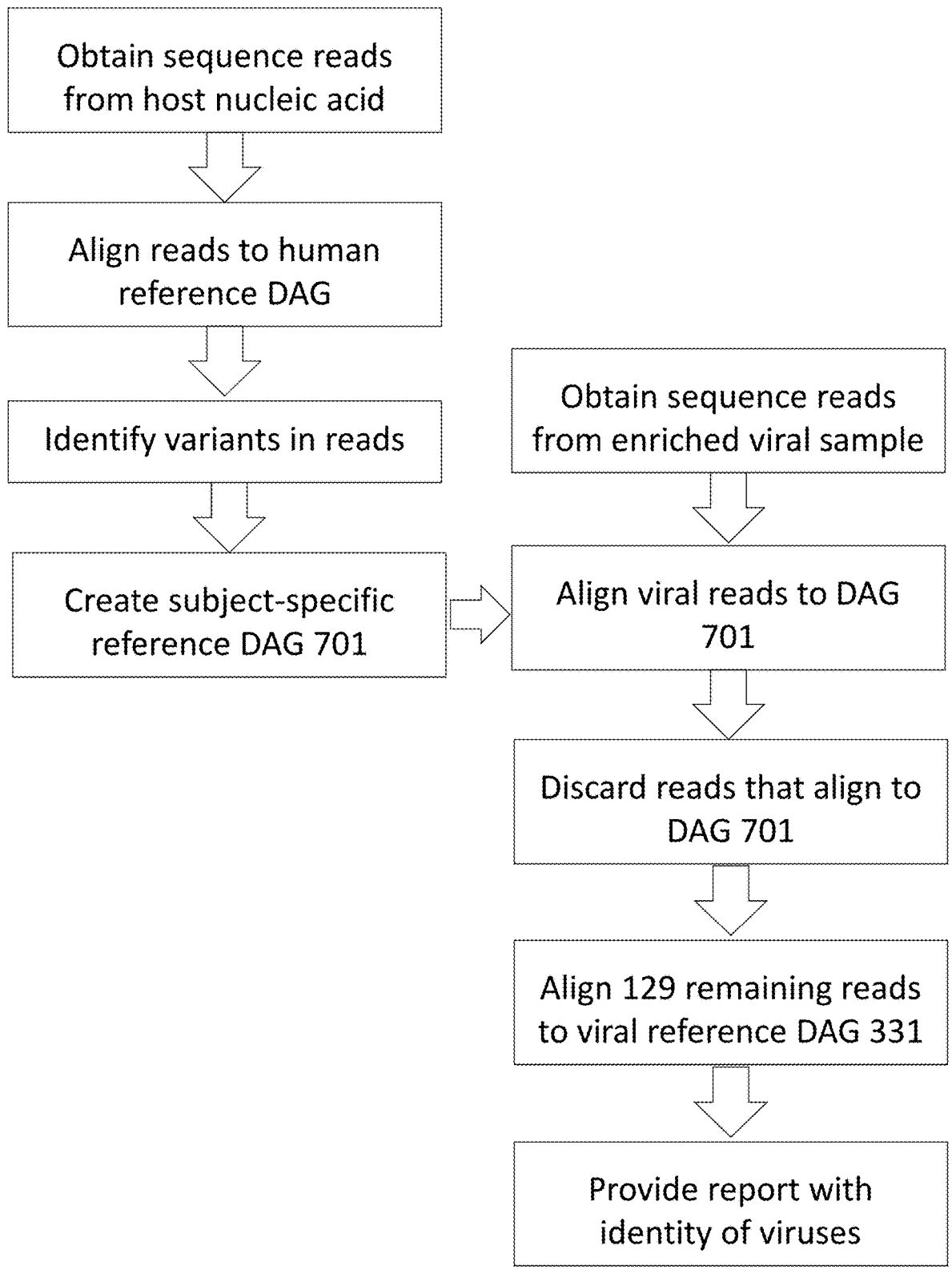
FIG. 7 shows the use of a subject-specific reference DAG.

FIG. 7 illustrates the use of a subject-specific reference DAG 701 within a process for the identification of species. First, reads (or, optionally, contigs of assembled reads) from a sample from the subject are aligned to a comprehensive human genome reference DAG. The sequence reads are aligned to a series of directed, acyclic human genome sequences (i.e., the human genome reference DAG) spanning branch points that account for all, or nearly-all, of the possible human genetic variation in the human reference DAG. The human reference DAG may first be assembled from available sequence databases, including "accepted" reference sequences and variant call format (VCF) entries. The reads are aligned to the human genome reference DAG using a multi-dimensional modified Smith-Waterman operation described below that greatly improves alignment accuracy and allows for sequence resolution not possible with conventional algorithms. For additional discussion, see U.S. Pub. 2015/0057946, incorporated by reference. This alignment of reads to the human reference DAG identifies variants.

A new subject-specific reference DAG 701 is created by adding all variants identified by aligning the reads to the reference as branches to the existing comprehensive reference DAG. Host nucleic acids are depleted from, and viral nucleic acids isolated in, a sample from the subject containing both viral and host nucleic acids, and viral nucleic acids are sequenced.

Reads from viral nucleic acids are aligned to the subject-specific reference DAG 701. Any reads that successfully align are discarded as host-derived reads. (Note: This step is optional, but is generally included because the prior depletion and isolation steps are frequently imperfect. Aligning to a comprehensive human reference DAG provides a more accurate way of filtering out remaining non-virus-derived sequences than existing methods such as matching assembled reads to known human or vertebrate sequences, which may under-match (due to individual-specific variants) or over-match (due to matches to sequences not actually present in the host)). Thus the subject-specific reference DAG may be used to exclude host-derived reads from comparison to viral reference genomes.

The remaining reads are compared to viral reference genomes by transforming those reference genomes 303 into a viral reference DAG 331. A viral reference DAG 331 is assembled from reference genomes 303 for each of a number of candidate virus families as described in connection with FIG. 3. A record is kept of which branches of the DAG 331 correspond to which reference virus species or strains (with some branches corresponding to multiple viral species or strains). Viral nucleic acid reads from the sample (preferably after excluding host-derived reads) are aligned to the viral reference DAG 331. (In certain embodiments, viral nucleic acid reads may be aligned to a plurality of viral reference DAGs representing variations among various viral genomes.)

Figure 8:
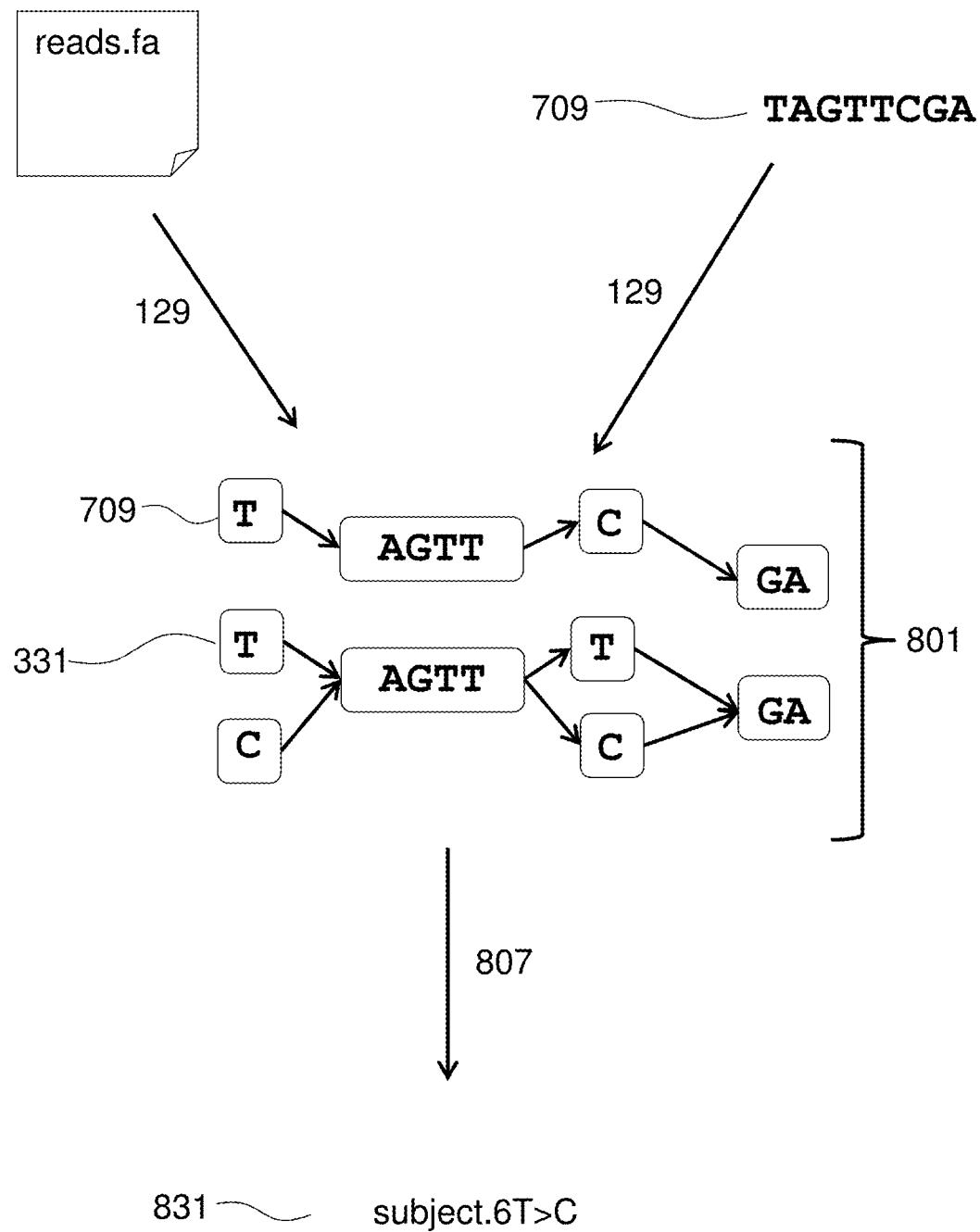
FIG. 8 illustrates finding alignments between a sequence and the viral reference DAG.

FIG. 8 illustrates finding 129 alignments 801 between the sequence reads ("reads.fa") (or a consensus sequence 209 from assembling the sequence reads) and the viral reference DAG 331. FIG. 8 also illustrates an optional variant calling 807 step to identify a subject genotype 831. Using alignment operations of the invention, reads can be rapidly mapped to the viral reference DAG 331 despite their large numbers or short lengths. Numerous benefits obtain by using a graph as a reference. For example, aligning against a graph is more accurate than aligning against a linear reference and then attempting to adjust one's results in light of other extrinsic information. This is primarily because the latter approach enforces an unnatural asymmetry between the sequence used in the initial alignment and other information. Aligning against an object that potentially represents all the relevant physical possibilities is much more computationally efficient than attempting to align against a linear sequence for each physical possibility (the number of such possibilities will generally be exponential in the number of junctions). A modified Smith-Waterman operation for comparing a sequence to a reference graph is provided here as an extension of pairwise alignment methods.

Pairwise alignment generally involves placing one sequence along part of target, introducing gaps according to an algorithm, scoring how well the two sequences match, and preferably repeating for various positions along the reference. The best-scoring match is deemed to be the alignment and represents an inference of homology between alignment portions of the sequences. In some embodiments, scoring an alignment of a pair of nucleic acid sequences involves setting values for the probabilities of substitutions and indels. When individual bases are aligned, a match or mismatch contributes to the alignment score by a substitution score, which could be, for example, 1 for a match and −0.33 for a mismatch. An indel deducts from an alignment score by a gap penalty, which could be, for example, −1. Gap penalties and substitution probabilities can be based on empirical knowledge or a priori assumptions about how sequences evolve. Their values affects the resulting alignment. Particularly, the relationship between the gap penalties and substitution probabilities influences whether substitutions or indels will be favored in the resulting alignment.

Stated formally, an alignment represents an inferred relationship between two sequences, x and y. For example, in some embodiments, an alignment A of sequences x and y maps x and y respectively to another two strings x' and y' that may contain spaces such that: (i)|x'|=|y'|; (ii) removing spaces from x' and y' should get back x and y, respectively; and (iii) for any i, x'[i] and y'[i] cannot be both spaces.

A gap is a maximal sub string of contiguous spaces in either x' or y'. An alignment A can include the following three kinds of regions: (i) matched pair (e.g., x[i]=y[i]; (ii) mismatched pair, (e.g., and both are not spaces); or (iii) gap (e.g., either x'[i . . . j] or y'[i . . . j] is a gap). In certain embodiments, only a matched pair has a high positive score a. In some embodiments, a mismatched pair generally has a negative score b and a gap of length r also has a negative score g+rs where g, s<0. For DNA, one common scoring scheme (e.g. used by BLAST) makes score a=1, score b=−3, g=−5 and s=−2. The score of the alignment A is the sum of the scores for all matched pairs, mismatched pairs and gaps. The alignment score of x and y can be defined as the maximum score among all possible alignments of x and y.

Any pair may have a score a defined by a 4×4 matrix B of substitution probabilities. For example, B(i,i)=1 and 0<B(i,j)<1 [for i≠j], is one possible scoring system. For instance, where a transition is thought to be more biologically probable than a transversion, matrix B could include B(C,T)=0.7 and B(A,T)=0.3, or other values desired or determined by methods known in the art.

A pairwise alignment, generally, involves—for sequence Q (query) having m characters and a reference genome T (target) of n characters—finding and evaluating possible local alignments between Q and T. For any 1≤i≤n and 1≤i≤m, the largest possible alignment score of T[h . . . i] and Q[k . . . j], where h≤i and k≤j, is computed (i.e. the best alignment score of any substring of T ending at position i and any substring of Q ending at position j). This can include examining all substrings with cm characters, where c is a constant depending on a similarity model, and aligning each substring separately with Q. Each alignment is scored, and the alignment with the preferred score is accepted as the alignment. One of skill in the art will appreciate that there are exact and approximate algorithms for sequence alignment. Exact algorithms will find the highest scoring alignment, but can be computationally expensive. Two well-known exact algorithms are Needleman-Wunsch (J Mol Biol, 48(3):443-453, 1970) and Smith-Waterman (J Mol Biol, 147(1):195-197, 1981; Adv. in Math. 20(3), 367-387, 1976). A further improvement to Smith-Waterman by Gotoh (J Mol Biol, 162(3), 705-708, 1982) reduces the calculation time from O(m^2n) to O(mn) where m and n are the sequence sizes being compared and is more amendable to parallel processing. In the field of bioinformatics, it is Gotoh's modified algorithm that is often referred to as the Smith-Waterman algorithm. Smith-Waterman approaches are being used to align larger sequence sets against larger reference sequences as parallel computing resources become more widely and cheaply available. See, e.g., Amazon's cloud computing resources. All of the journal articles referenced herein are incorporated by reference in their entireties.

The original Smith-Waterman (SW) algorithm aligns linear sequences by rewarding overlap between bases in the sequences, and penalizing gaps between the sequences. Smith-Waterman also differs from Needleman-Wunsch, in that SW does not require the shorter sequence to span the string of letters describing the longer sequence. That is, SW does not assume that one sequence is a read of the entirety of the other sequence. Furthermore, because SW is not obligated to find an alignment that stretches across the entire length of the strings, a local alignment can begin and end anywhere within the two sequences.

The original SW algorithm is expressed for an n×m matrix H, representing the two strings of length n and m, in terms of equation (1):

$$H\_k0 = H\_0l = 0 \text{ (for } 0 \leq k \leq n \text{ and } 0 \leq l \leq m) \quad (1)$$

$$H\_ij = \max\{H(i-1,j-1) + s(a\_i, b\_j), H\_(i-1,j) - W\_in, H\_(i,j-1) - W\_del, 0\} \text{ (for } 1 \leq i \leq n \text{ and } 1 \leq i \leq m)$$

In the equations above, s(ai,bj) represents either a match bonus (when ai=bj) or a mismatch penalty (when ai≠bj), and insertions and deletions are given the penalties Win and Wdel, respectively. In most instances, the resulting matrix has many elements that are zero. This representation makes it easier to backtrace from high-to-low, right-to-left in the matrix, thus identifying the alignment.

Once the matrix has been fully populated with scores, the SW algorithm performs a backtrack to determine the alignment. Starting with the maximum value in the matrix, the algorithm will backtrack based on which of the three values (Hi−1,j−1, Hi−1,j, or Hi,j−1) was used to compute the final maximum value for each cell. The backtracking stops when a zero is reached. The optimal-scoring alignment may contain greater than the minimum possible number of insertions and deletions, while containing far fewer than the maximum possible number of substitutions.

SW or SW-Gotoh may be implemented using dynamic programming to perform local sequence alignment of the two strings, S and A, of sizes m and n, respectively. This dynamic programming employs tables or matrices to preserve match scores and avoid re-computation for successive cells. Each element of the string can be indexed with respect to a letter of the sequence, that is, if S is the string ATCGAA, S[1]=A.

Instead of representing the optimum alignment as Hi,j (above), the optimum alignment can be represented as B[j,k] in equation (2) below:

$$B[j,k] = \max(p[j,k], i[j,k], d[j,k], 0) \text{ (for } 0 \leq j \leq m, 0 \leq k \leq n) \quad (2)$$

The arguments of the maximum function, B[j,k], are outlined in equations (3)-(5) below, wherein MISMATCH_PEN, MATCH_BONUS, INSERTION_PEN, DELETION_PEN, and OPENING_PEN are all constants, and all negative except for MATCH_BONUS (PEN is short for PENALTY). The match argument, p[j,k], is given by equation (3), below:

$$\begin{aligned}p[j,k] &= \max(p[j-1,k-1], i[j-1,k-1], d[j-1,k-1]) + \\ &\quad \text{MISMATCH\_PEN, if } S[j] \neq A[k] \\ &= \max(p[j-1,k-1], i[j-1,k-1], d[j-1,k-1]) + \\ &\quad \text{MATCH\_BONUS, if } S[j] = A[k]\end{aligned} \quad (3)$$

the insertion argument i[j,k], is given by equation (4), below:

$$i[j,k] = \max(p[j-1,k] + \text{OPENING\_PEN}, i[j-1,k], d[j-1,k] + \text{OPENING\_PEN}) + \text{INSERTION\_PEN} \quad (4)$$

and the deletion argument d[j,k], is given by equation (5), below:

$$d[j,k] = \max(p[j,k-1] + \text{OPENING\_PEN}, i[j,k-1] + \text{OPENING\_PEN}, d[j,k-1]) + \text{DELETION\_PEN} \quad (5)$$

For all three arguments, the [0,0] element is set to zero to assure that the backtrack goes to completion, i.e., p[0,0]=i[0,0]=d[0,0]=0.

The scoring parameters are somewhat arbitrary, and can be adjusted to achieve the behavior of the computations. One example of the scoring parameter settings (Huang, Chapter 3: Bio-Sequence Comparison and Alignment, ser. Curr Top Comp Mol Biol. Cambridge, Mass.: The MIT Press, 2002) for DNA would be:

MATCH_BONUS: 10
MISMATCH_PEN: −20
INSERTION_PEN: −40
OPENING_PEN: −10
DELETION_PEN: −5

The relationship between the gap penalties (INSERTION_ PEN, OPENING_PEN) above help limit the number of gap openings, i.e., favor grouping gaps together, by setting the gap insertion penalty higher than the gap opening cost. Of course, alternative relationships between MISMATCH_ PEN, MATCH_BONUS, INSERTION_PEN, OPENING_ PEN and DELETION_PEN are possible.

In some embodiments, the methods and systems of the invention use a modified Smith-Waterman operation that involves a multi-dimensional look-back through the viral reference DAG 331. Multi-dimensional operations of the invention provide for a "look-back" type analysis of sequence information (as in Smith-Waterman), wherein the look back is conducted through a multi-dimensional space that includes multiple pathways and multiple nodes. The multi-dimensional algorithm can be used to align sequence reads against the graph-type reference. That alignment algorithm identifies the maximum value for Ci,j by identifying the maximum score with respect to each sequence contained at a position on the graph. In fact, by looking "backwards" at the preceding positions, it is possible to identify the optimum alignment across a plurality of possible paths.

The modified Smith-Waterman operation described here, aka the multi-dimensional alignment, provides exceptional speed when performed in a genomic graph system that employs physical memory addressing (e.g., through the use of native pointers or index free adjacency as discussed above). The combination of multi-dimensional alignment to a graph 331 with the use of spatial memory addresses (e.g., native pointers or index-free adjacency) improves what the computer system is capable of, facilitating whole genomic scale analysis to be performed using the methods described herein.

The operation includes aligning a sequence, or string, to a graph. For the purpose of defining the algorithm, let S be the string being aligned, and let D be the directed graph to which S is being aligned. The elements of the string, S, are bracketed with indices beginning at 1. Thus, if S is the string ATCGAA, S[1]=A, S[4]=G, etc.

In certain embodiments, for the graph, each letter of the sequence of a node will be represented as a separate element, d. In a preferred embodiment, node or edge objects contain the sequences and the sequences are stored as the longest-possible string in each object. A predecessor of d is defined as:

(i) If d is not the first letter of the sequence of its object, the letter preceding d in its object is its (only) predecessor;

(ii) If d is the first letter of the sequence of its object, the last letter of the sequence of any object that is a parent of d's object is a predecessor of d.

The set of all predecessors is, in turn, represented as P[d].

In order to find the "best" alignment, the algorithm seeks the value of M[0], the score of the optimal alignment of the first j elements of S with the portion of the graph preceding (and including) d. This step is similar to finding Hi,j in equation 1 above. Specifically, determining M[j,d] involves finding the maximum of a, i, e, and 0, as defined below:

$$M[j,d]=\max\{a,i,e,0\} \quad (6)$$

where e=max{M[j, p*]+DELETE_PEN} for p* in P[d]
i=M[j−1, d]+INSERT_PEN
a=max{M[j−1, p*]+MATCH_SCORE} for p* in P[d], if S[j]=d;
max{M[j−1, p*]+MISMATCH_PEN} for p* in P[d], if S[j]≠d As described above, e is the highest of the alignments of the first j characters of S with the portions of the graph up to, but not including, d, plus an additional DELETE_PEN. Accordingly, if d is not the first letter of the sequence of the object, then there is only one predecessor, p, and the alignment score of the first j characters of S with the graph (up-to-and-including p) is equivalent to M[j,p]+DELETE_PEN. In the instance where d is the first letter of the sequence of its object, there can be multiple possible predecessors, and because the DELETE_PEN is constant, maximizing [M[j, p*]+DELETE_PEN] is the same as choosing the predecessor with the highest alignment score with the first j characters of S.

In equation (6), i is the alignment of the first j−1 characters of the string S with the graph up-to-and-including d, plus an INSERT_PEN, which is similar to the definition of the insertion argument in SW (see equation 1).

Additionally, a is the highest of the alignments of the first j characters of S with the portions of the graph up to, but not including d, plus either a MATCH_SCORE (if the jth character of S is the same as the character d) or a MISMATCH_PEN (if the jth character of S is not the same as the character d). As with e, this means that if d is not the first letter of the sequence of its object, then there is only one predecessor, i.e., p. That means a is the alignment score of the first j−1 characters of S with the graph (up-to-and-including p), i.e., M[j−1,p], with either a MISMATCH_PEN or MATCH_SCORE added, depending upon whether d and the jth character of S match. In the instance where d is the first letter of the sequence of its object, there can be multiple possible predecessors. In this case, maximizing {M[j, p*]+MISMATCH_PEN or MATCH_SCORE} is the same as choosing the predecessor with the highest alignment score with the first j−1 characters of S (i.e., the highest of the candidate M[j−1,p*] arguments) and adding either a MISMATCH_PEN or a MATCH_SCORE depending on whether d and the jth character of S match.

Again, as in the SW algorithm, the penalties, e.g., DELETE_PEN, INSERT_PEN, MATCH_SCORE and MISMATCH_PEN, can be adjusted to encourage alignment with fewer gaps, etc.

As described in the equations above, the operation finds the optimal (e.g., maximum) value for a sequence reads 205 to the viral reference DAG 331 by calculating not only the insertion, deletion, and match scores for that element, but looking backward (against the direction of the graph) to any prior nodes on the graph to find a maximum score.

Figure 9:
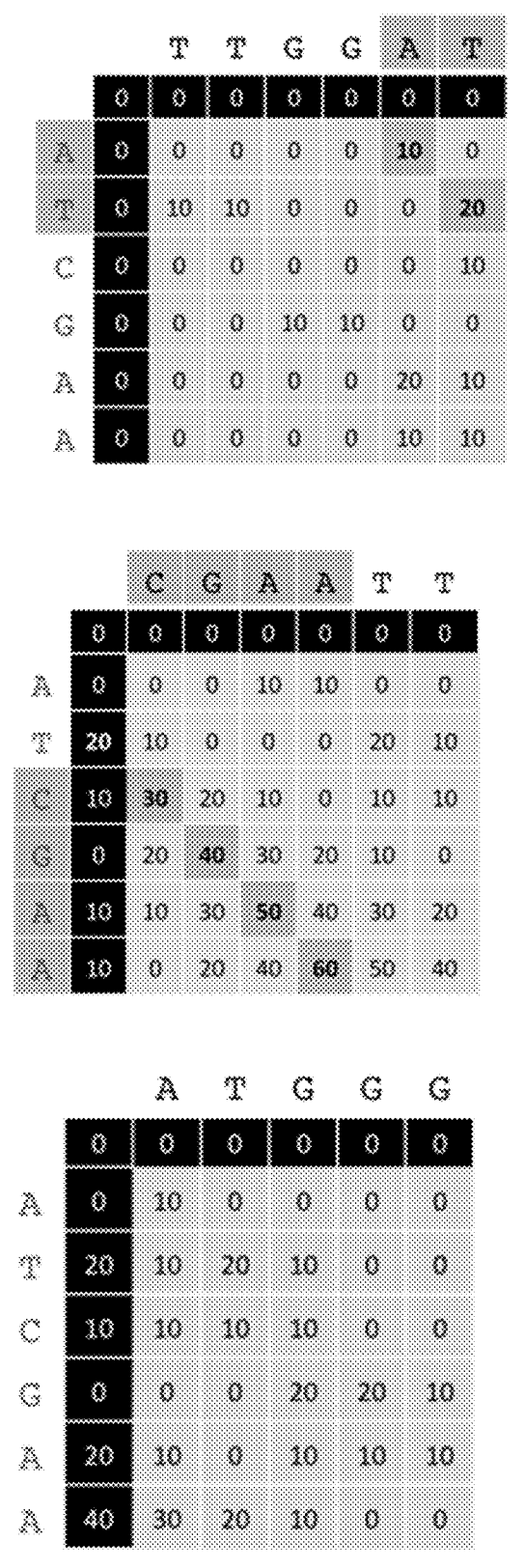

FIG. 9 shows the matrices that represent the comparison. The modified Smith-Waterman operation of the invention identifies the highest score and performs a backtrack to identify the proper alignment of the sequence. See, e.g., U.S. Pub. 2015/0057946 and U.S. Pub. 2015/0056613, both incorporated by reference. Systems and methods of the invention can be used to provide a report that identifies a modified base at the position within the genome of the subject. Other information may be found in Kehr et al., 2014, Genome alignment with graph data structures: a comparison, BMC Bioinformatics 15:99 and Lee, 2003, Generating consensus sequences from partial order multiple sequence alignment graphs, Bioinformatics 19(8):999-1008, both incorporated by reference. Thus, identifying a virus for the viral nucleic acid from the sample 203 may include aligning 129 one or more of the sequence reads 205 to the viral reference DAG 331 as shown in FIG. 8. The branches to which the reads 205 have been aligned are identified, along with the corresponding species or strain of virus.

Figure 10:
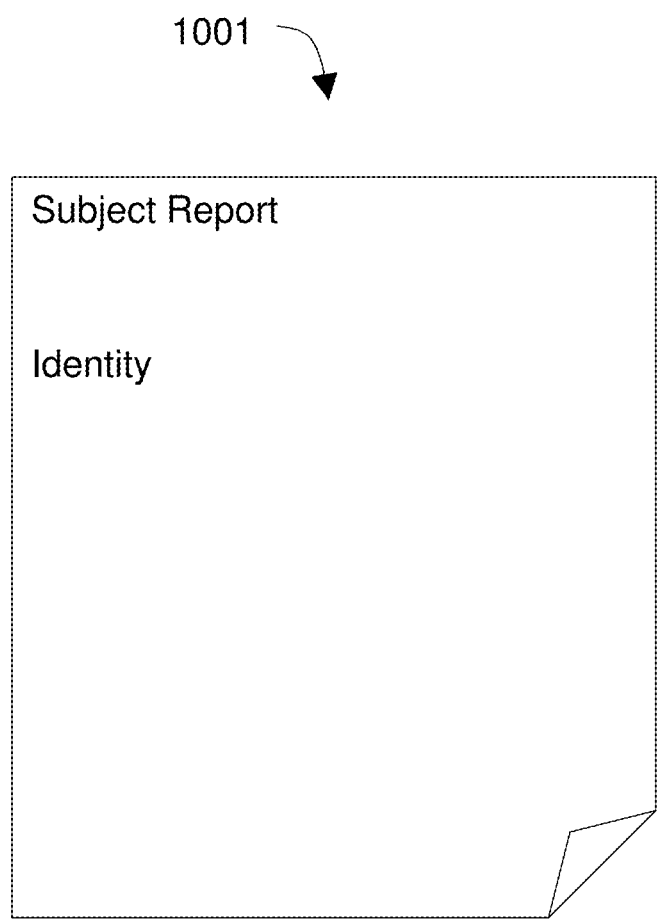
FIG. 10 illustrates a report that identifies a virus.

FIG. 10 illustrates a report 1001 that may be generated by the system 401. Preferably the report 1001 includes at least the identity of a virus for the viral nucleic acid from the sample 203. The report 1001 will preferably include a list of the viral species or strains corresponding to the branches of the viral reference DAG 331 to which the reads 205 aligned, along with the percentage of reads aligned (or percentage of nucleotides matched) to each.

Additionally, branches (and thus species) may be weighted according to the "delta" between the branch and the next-best alignment for a given read. Thus systems and methods of the invention can be used to produce a report that includes the identity of any virus successfully detected in the sample.

Additionally and in some embodiments, systems and methods of the invention may be used to characterize quasispecies. For the characterization of quasispecies, reads from a sample (such as the sample 203 of FIG. 2) from the subject are aligned to a comprehensive human reference DAG to identify variants in the reads as described above. As described above, a new subject-specific reference DAG is created by adding all variants identified in the reads as branches to the existing comprehensive reference DAG. Host nucleic acids are depleted from and viral nucleic acids isolated in a sample from the subject containing both viral and host nucleic acids, and viral nucleic acids are sequenced 213.

Reads 205 from viral nucleic acids are aligned to the subject-specific reference DAG. Any reads that successfully align may be discarded as host-derived reads, since the prior depletion and isolation steps may be imperfect. This step is optional, but may be included where depletion and isolation steps are imperfect.

A viral reference DAG 331 is assembled from reference genomes for the target virus (e.g., influenza or HIV, both of which are characterized by high intra-host heterogeneity). A record is kept of which branches of the DAG 331 correspond to which reference virus strains (with some branches corresponding to multiple strains). Viral nucleic acid reads (such as the reads 205 of FIG. 2) from the sample are aligned 129 to the viral reference DAG 331. The branches to which the reads have been aligned are identified, along with the corresponding strains of virus. Each full path in an alignment may be taken to represent a nucleic acid from a member of the viral quasispecies. All of the closely-related paths found in the alignment may be taken to represent the quasispecies as found by sequencing the sample 203. Thus, the system and method may be used to provide a description of the virus as a quasispecies (e.g., rather than to simply identify by species or strain name). It is additionally noted that one suitable way to describe a quasispecies is to present it as a DAG. Thus a report may be produced that includes a DAG showing a quasispecies.

Figure 11:
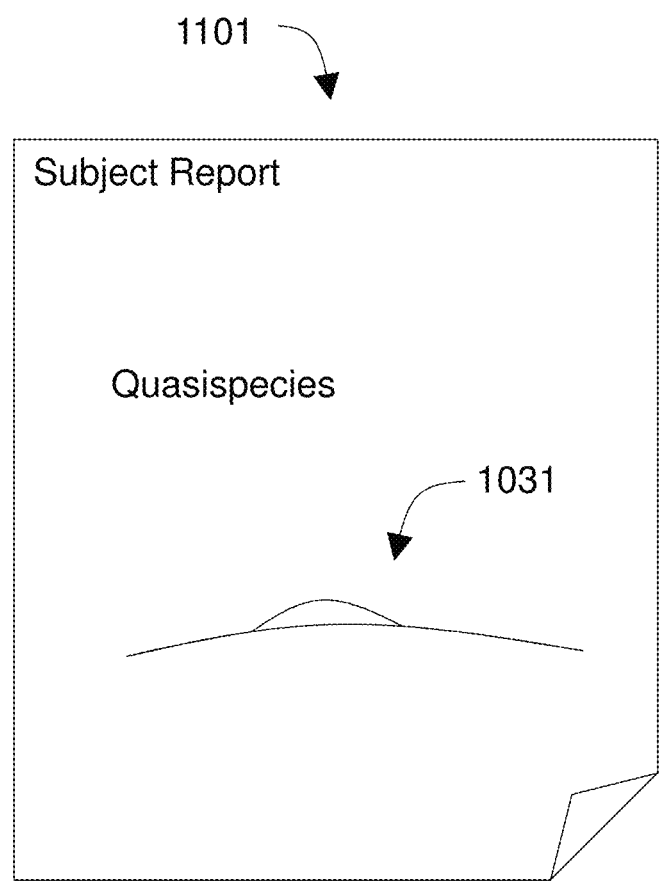
FIG. 11 illustrates a report that characterizes a quasispecies.

FIG. 11 illustrates a report 1101 that may be produced using systems and methods of the invention to characterize a quasispecies. The report 1101 may include a quasispecies DAG 1131 that illustrates the quasispecies as found to be present in the nucleic acid in the sample 203. The report may optionally include variant calls (such as the variant calls 831 of FIG. 8) to describe variants defining members of the quasispecies (e.g., as defined as variants of a published reference for a most-closely related virus species or strain). While the quasispecies DAG 1131 itself represents the full genetic variety fond in the sample 203, it may still be convenient or desirable to pull out variant calls 831 for the purposes of, for example, comparing to literature or databases or as inputs to predictive software that predict pathogenicity or MHC binding of gene products.

Preferably, the report 1101 includes a list of strains, when more than one is present, as well as the DAG 1131 representing the aligned reads, including de novo variants identified in the alignment process. Due to the heterogeneous nature of the population a consensus linear sequence may not obtain. Optionally, a threshold may be imposed to filter out variants/alternative paths that are supported by few enough reads that it is not possible to determine with any confidence that they don't represent read errors.

Additionally and alternatively, systems and methods of the invention may be used for the discovery of virus-derived sequences in tumor genomes.

DAGs can be used for identifying mutations that are induced by, or associated with, disease, especially cancer. Specific changes associated with advanced stages of a disease may be easily differentiated from lesser diseased cells, thus providing insight into the relationship between the size and location of the mutations and progression of the disease. Those insights can be used to identify disease progression in other patients, and the relationship also provides for faster and more accurate typing of samples later collected from the same patient to monitor for disease progression or recurrence. See U.S. Pub. 2015/0197815, incorporated by reference. Thus, the use of DAGs can improve the accuracy of the assembly of tumor-cell genomes and the discovery of tumor-specific mutations. Some forms of cancer have been found to be associated not with spontaneously-occurring mutations, but rather with genetic content introduced by viruses in the course of their hijacking of cellular machinery to serve their own replication. See HPV for one well-known example.

When a viral etiology is suspected, identification of virus-derived sequences in the genomes of tumor samples can aid in confirming viral etiology and identifying the responsible virus. Use of methods described here can yield significant benefits in identifying such sequences.

To identify virus-derived sequences in the genome of a tumor sample, reads from a sample from the subject's normal genome (a sample from non-cancerous cells) are first preferably aligned to a comprehensive human reference DAG to identify variants. A new subject-specific reference DAG is created by adding all variants identified as branches to the existing comprehensive reference DAG.

Reads from a sample from the subject's cancerous cells are aligned to the subject-specific reference DAG. Reads that do not align and reads representing variants from the assembly of the reads from the normal genome are considered candidate reads (i.e., potentially pathological and/or virally-derived). Other reads are discarded.

Candidate reads are aligned to viral reference DAGs 331, particularly those for virus families associated with cancer such as polyomavirus and papillomavirus, and typed as described above herein. Where alignments between the sequence reads 205 and a viral reference DAG 331 are found, a report may be provided that includes the identity of the virus that has thus been found in the subject's cancerous cells. For other discussion see Barzon et al., 2011, Applications of next-generation sequencing technologies to diagnostic virology, Int J Mol Sci 12(11):7861-7884 and Van den Hoecke et al., 2015, Analysis of the genetic diversity of influenza A viruses using next-generation sequencing, BMC Genomics 16:79, the contents of each of which are incorporated by reference.

As discussed above briefly in connection with FIG. 2, optionally, systems and methods of the invention may be used for variant calling 807 to produce genotype information 831 about a viral genome. The variant calling can include aligning sequence reads to the graph and reporting SNP alleles in a format such as a Sequence Alignment Map (SAM) or a Variant Call Format (VCF) file. Some background may be found in Li & Durbin, 2009, Fast and accurate short read alignment with Burrows-Wheeler Transform. Bioinformatics 25:1754-60 and McKenna et al., 2010, The Genome Analysis Toolkit: a MapReduce framework for analyzing next-generation DNA sequencing data, Genome Res 20(9):1297-1303, the contents of each of which are incorporated by reference. Variant calling 831 produces results ("variant calls") that may be stored as a sequence alignment map (SAM) or binary alignment map (BAM) file—comprising an alignment string (the SAM format is described, e.g., in Li, et al., The Sequence Alignment/Map format and SAMtools, Bioinformatics, 2009, 25(16):2078-9). Additionally or alternatively, output from the variant calling may be provided in a variant call format (VCF) file, e.g., in report 1001. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. Further discussion may be found in U.S. Pub. 2013/0073214; U.S. Pub. 2013/0345066; U.S. Pub. 2013/0311106; U.S. Pub. 2013/0059740; U.S. Pub. 2012/

0157322; U.S. Pub. 2015/0057946 and U.S. Pub. 2015/0056613, each incorporated by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for analyzing a virus, the method comprising using at least one hardware processor connected to a tangible memory subsystem to perform:
   obtaining a plurality of sequence reads from a sample containing viral nucleic acid;
   creating, in the tangible memory subsystem, a viral DNA reference graph representing a plurality of known viral sequences, the viral DNA reference graph comprising a directed acyclic graph (DAG) comprising a plurality of vertices stored as objects in the tangible memory subsystem, wherein sequence strings of the known viral sequences that match each other when aligned are each represented by a single object and sequence strings that vary are represented as alternate objects, wherein at least one sequence string comprises a plurality of symbols, and wherein each object is stored in the tangible memory subsystem as a sequence string and a list of one or more pointers to adjacent objects, wherein each pointer identifies a physical location in the tangible memory subsystem at which an adjacent object is stored, such that the objects are linked to represent each of the known viral sequences as a path through the viral DNA reference graph;
   aligning the sequence reads to paths through the viral DNA reference graph, wherein the aligning comprises calculating match scores between a sequence read and a sequence string associated with each vertex, and looking backwards at each vertex to predecessor vertices if and only if a symbol comprises the first symbol of the sequence string associated with its vertex to select a path with an optimal score;
   retrieving, based on the aligned sequence reads to paths through the viral DNA reference graph, an identity of a virus for the one of the plurality of known viral sequences; and
   providing a report that includes the identity of the virus.

2. The method of claim 1, wherein creating a viral DNA reference graph further comprises:
   obtaining the plurality of known viral sequences from an online sequence database;
   finding and deleting redundancies among homologous portions of the known viral sequences, leaving the segments of the known viral sequences that match each other when aligned and segments of the known viral sequences that vary; and
   creating one of the objects in the tangible memory subsystem for each of the segments.

3. The method of claim 1, wherein the directed graph represents a plurality of known variations in a viral genome, in which each of the known variations is associated with a path through the directed graph.

4. The method of claim 1, further comprising retrieving, based on the alignments, an identity of a plurality of viruses for the sample.

5. The method of claim 4, wherein the report includes a list of viral species or strains determined based on the retrieved identities, and the report further quantifies an amount of each viral species or strain present in the viral nucleic acid.

6. The method of claim 4, wherein the known viral sequences are of the same species as the viral nucleic acid, the method further comprising characterizing a quasispecies of the virus in the sample.

7. The method of claim 6, wherein the report includes a list of strains of the virus and a graphical representation of a graph of aligned sequence reads from the sample.

8. The method of claim 1, further comprising:
   obtaining sequence reads from genomic nucleic acid from a healthy cell of a subject;
   aligning the sequence reads to a human reference graph;
   identifying, based on the aligned sequence reads, a plurality of variants;
   creating a subject-specific reference graph that includes the plurality of variants;
   obtaining disease sequence reads from a diseased cell of the subject and aligning them to the subject-specific reference graph, wherein disease sequence reads that do not align and disease sequence reads that contain variants relative to the subject-specific reference DAG are considered candidate reads; and
   aligning the candidate reads to the directed graph representing known viral sequences.

9. The method of claim 8, wherein the report includes the identities of one or more viruses identified by aligning the candidate reads to the directed graph representing known viral sequences.

10. The method of claim 1, wherein the sequence from the sample comprises a sequence read created by sequencing the viral nucleic acid using a sequencing instrument.

11. The method of claim 1, further comprising depleting host-specific nucleic acids from the sample.

12. The method of claim 1, wherein objects of the viral DNA reference graph comprise vertex objects connected by edge objects and an adjacency list for each vertex object and edge object, wherein the adjacency list for a vertex object or edge object lists the edge objects or vertex objects to which that vertex object or edge object is adjacent, wherein each entry in an adjacency list is a pointer to the adjacent vertex object or edge object, wherein each pointer identifies a physical location in the memory subsystem at which the adjacent object is stored.

13. The method of claim 1, wherein the viral DNA reference graph uses index-free adjacency to link the objects into paths to represent the plurality of known viral sequences.

14. The method of claim 1, wherein converting the sequence into the alignment comprises using the processor to perform a multi-dimensional look-back operation to find a highest-scoring trace through a multi-dimensional matrix.

15. The method of claim 1, wherein creating the viral DNA reference graph comprises:
associating an initial object with a sequence string representing one of the known viral sequences;
dividing the initial object into multiple objects at positions in which known variations from the plurality of known viral sequences occur; and
connecting the plurality of objects to create paths such that there is a path for each known variation.

16. A system for analyzing a virus, the system comprising a processor coupled to a tangible memory subsystem, wherein the tangible memory subsystem contains instructions that when executed by the processor cause the system to perform:
obtaining a plurality of sequence reads from a sample containing viral nucleic acid;
creating, in the tangible memory subsystem, a viral DNA reference graph representing a plurality of known viral sequences, the viral DNA reference graph comprising a directed acyclic graph (DAG) comprising a plurality of vertices stored as objects in the tangible memory subsystem, wherein sequence strings of the known viral sequences that match each other when aligned are each represented by a single object and sequence strings that vary are represented as alternate objects, and wherein each object is stored in the tangible memory subsystem as a sequence string and a list of one or more pointers to adjacent objects, wherein each pointer identifies a physical location in the tangible memory subsystem at which an adjacent object is stored, such that the objects are linked to represent each of the known viral sequences as a path through the viral DNA reference graph;
aligning the sequence reads to paths through the viral DNA reference graph, wherein the aligning comprises calculating match scores between a sequence read and a sequence string associated with each vertex, and looking backwards at each vertex to predecessor vertices if and only if a symbol comprises the first symbol of the sequence string associated with its vertex to select a path with an optimal score;
retrieving, based on the aligned sequence reads to paths through the viral DNA reference graph, an identity of a virus for each of the plurality of sequences; and
providing, via an input/output device coupled to the processor, a report that includes the retrieved identities.

17. The system of claim 16, further operable to:
obtain the plurality of known viral sequences from an online sequence database;
find and delete redundancies among homologous portions of the known viral sequences, leaving the segments of the known viral sequences that match each other when aligned and segments of the known viral sequences that vary; and
create one of the objects in the tangible memory subsystem for each of the segments.

18. The system of claim 16, wherein host-derived sequence reads are removed from the sample prior to finding alignments.

19. The system of claim 16, further operable to:
obtain sequence reads from genomic nucleic acid from a healthy cell of a subject;
align the sequence reads to a human reference graph;
identify, based on the aligned sequence reads, a plurality of variants;
create a subject-specific reference graph that includes the plurality of variants;
obtain tumor-associated sequence reads from a tumor of the subject;
align the tumor-associated sequence reads to the subject-specific reference graph; and
align tumor-associated reads that do not align to the subject-specific reference graph to the directed graph representing a plurality of known viral sequences.

20. The system of claim 16, wherein the report includes a list of viral species or strains determined based on the retrieved identities, and the report further quantifies an amount of each viral species or strain present in the viral nucleic acid.

* * * * *